US010709830B2

(12) United States Patent
Tanner et al.

(10) Patent No.: US 10,709,830 B2
(45) Date of Patent: *Jul. 14, 2020

(54) REDUCED ROTATIONAL MASS MOTOR ASSEMBLY FOR CATHETER PUMP

(71) Applicant: TC1 LLC, Pleasanton, CA (US)

(72) Inventors: Adam R. Tanner, Mountain View, CA (US); Paul F. Muller, San Carlos, CA (US); Alan Schenck, Sunnyvale, CA (US); Michael R. Butler, Dublin, CA (US); Todd Jenkins, San Jose, CA (US)

(73) Assignee: TC1 LLC, Pleasanton, CA (US)

( * ) Notice: Subject to any disclaimer, the term of this patent is extended or adjusted under 35 U.S.C. 154(b) by 189 days.

This patent is subject to a terminal disclaimer.

(21) Appl. No.: 15/635,531

(22) Filed: Jun. 28, 2017

(65) Prior Publication Data

US 2017/0319764 A1 Nov. 9, 2017

Related U.S. Application Data

(63) Continuation of application No. 15/003,576, filed on Jan. 21, 2016, now Pat. No. 9,770,543.

(Continued)

(51) Int. Cl.
*A61M 1/12* (2006.01)
*A61M 1/10* (2006.01)
*A61M 25/09* (2006.01)

(52) U.S. Cl.
CPC ............ *A61M 1/125* (2014.02); *A61M 1/102* (2014.02); *A61M 1/1013* (2014.02);
(Continued)

(58) Field of Classification Search
CPC .............................. A61M 1/122; A61M 1/125
See application file for complete search history.

(56) References Cited

U.S. PATENT DOCUMENTS 2,789,511 A 4/1957 Doble
3,510,229 A 5/1970 Smith
(Continued)

FOREIGN PATENT DOCUMENTS

CA 2701810 A1 4/2009
EP 0453234 A1 10/1991
(Continued)

OTHER PUBLICATIONS

Abiomed, "Impella 5.0 with the Impella Console, Circulatory Support System, Instructions for Use & Clinical Reference Manual," Jun. 2010, in 122 pages.
(Continued)

*Primary Examiner* — Michael W Kahelin
(74) *Attorney, Agent, or Firm* — Armstrong Teasdale LLP

(57) ABSTRACT

A catheter pump is disclosed. The catheter pump can include an impeller and a catheter body having a lumen in which waste fluid flows proximally therethrough during operation of the catheter pump. The catheter pump can also include a drive shaft disposed inside the catheter body. A motor assembly can include a chamber. The motor assembly can include a rotor disposed in the at least a portion of the chamber, the rotor mechanically coupled with a proximal portion of the drive shaft such that rotation of the rotor causes the drive shaft to rotate, the rotor including a longitudinal rotor lumen therethrough. The motor assembly can also comprise a stator assembly disposed about the rotor. During operation of the catheter pump, the waste fluid flows from the lumen into the chamber such that at least a portion of the waste fluid flows proximally through the longitudinal rotor lumen.

16 Claims, 10 Drawing Sheets

Related U.S. Application Data

(60) Provisional application No. 62/106,670, filed on Jan. 22, 2015.

(52) U.S. Cl.
CPC ........ *A61M 1/1034* (2014.02); *A61M 1/1036* (2014.02); *A61M 1/122* (2014.02); *A61M 25/09* (2013.01); A61M 1/101 (2013.01); A61M 1/1008 (2014.02); A61M 1/1012 (2014.02); A61M 1/1024 (2014.02); A61M 2205/3317 (2013.01); A61M 2205/3606 (2013.01); A61M 2205/366 (2013.01); A61M 2205/3666 (2013.01)

(56) References Cited

U.S. PATENT DOCUMENTS

| | | | |
|---|---|---|---|
| 3,995,617 A | 12/1976 | Watkins et al. | |
| 4,115,040 A | 9/1978 | Knorr | |
| 4,129,129 A | 12/1978 | Amrine | |
| 4,135,253 A | 1/1979 | Reich et al. | |
| 4,143,425 A | 3/1979 | Runge | |
| 4,304,524 A | 12/1981 | Coxon | |
| D264,134 S | 4/1982 | Xanthopoulos | |
| 4,382,199 A | 5/1983 | Isaacson | |
| 4,458,366 A | 7/1984 | MacGregor et al. | |
| 4,537,561 A | 8/1985 | Xanthopoulos | |
| 4,589,822 A | 5/1986 | Clausen et al. | |
| 4,625,712 A * | 12/1986 | Wampler ............ | A61M 1/102 128/DIG. 3 |
| 4,673,334 A | 6/1987 | Allington et al. | |
| 4,686,982 A | 8/1987 | Nash | |
| 4,696,667 A | 9/1987 | Masch | |
| 4,704,121 A | 11/1987 | Moise | |
| 4,753,221 A | 6/1988 | Kensey et al. | |
| 4,817,586 A | 4/1989 | Wampler | |
| 4,846,152 A | 7/1989 | Wampler et al. | |
| 4,895,557 A * | 1/1990 | Moise ................ | A61M 1/1017 415/900 |
| 4,900,227 A | 2/1990 | Trouplin | |
| 4,902,272 A | 2/1990 | Milder et al. | |
| 4,906,229 A | 3/1990 | Wampler | |
| 4,908,012 A | 3/1990 | Moise et al. | |
| 4,919,647 A | 4/1990 | Nash | |
| 4,927,407 A * | 5/1990 | Dorman ................ | F04D 13/06 415/112 |
| 4,944,722 A | 7/1990 | Carriker et al. | |
| 4,957,504 A | 9/1990 | Chardack | |
| 4,964,864 A | 10/1990 | Summers et al. | |
| 4,969,865 A | 11/1990 | Hwang et al. | |
| 4,985,014 A | 1/1991 | Orejola | |
| 5,021,048 A | 6/1991 | Buckholtz | |
| 5,044,902 A | 9/1991 | Malbec | |
| 5,045,072 A | 9/1991 | Castillo et al. | |
| 5,049,134 A | 9/1991 | Golding et al. | |
| 5,059,174 A | 10/1991 | Vaillancourt | |
| 5,061,256 A | 10/1991 | Wampler | |
| 5,089,016 A | 2/1992 | Millner et al. | |
| 5,098,256 A | 3/1992 | Smith | |
| 5,163,910 A | 11/1992 | Schwartz et al. | |
| 5,169,378 A | 12/1992 | Figuera | |
| 5,171,212 A | 12/1992 | Buck et al. | |
| 5,190,528 A | 3/1993 | Fonger et al. | |
| 5,195,960 A | 3/1993 | Hossain et al. | |
| 5,211,546 A | 5/1993 | Isaacson et al. | |
| 5,221,270 A | 6/1993 | Parker | |
| 5,234,407 A | 8/1993 | Teirstein et al. | |
| 5,234,416 A | 8/1993 | MacAulay et al. | |
| 5,290,227 A | 3/1994 | Pasque | |
| 5,300,112 A | 4/1994 | Barr | |
| 5,344,443 A | 9/1994 | Palma et al. | |
| 5,376,114 A | 12/1994 | Jarvik | |
| 5,393,207 A | 2/1995 | Maher et al. | |
| 5,405,341 A | 4/1995 | Martin | |
| 5,437,541 A | 8/1995 | Vainrub | |
| 5,458,459 A | 10/1995 | Hubbard et al. | |
| 5,490,763 A | 2/1996 | Abrams et al. | |
| 5,527,159 A | 6/1996 | Bozeman, Jr. et al. | |
| 5,534,287 A | 7/1996 | Lukic | |
| 5,586,868 A | 12/1996 | Lawless et al. | |
| 5,613,935 A | 3/1997 | Jarvik | |
| 5,725,513 A | 3/1998 | Ju et al. | |
| 5,735,897 A | 4/1998 | Buirge | |
| 5,741,234 A | 4/1998 | Aboul-Hosn | |
| 5,746,709 A | 5/1998 | Rom et al. | |
| 5,749,855 A | 5/1998 | Reitan | |
| 5,776,161 A | 7/1998 | Globerman | |
| 5,779,721 A | 7/1998 | Nash | |
| 5,824,070 A | 10/1998 | Jarvik | |
| 5,859,482 A | 1/1999 | Crowell et al. | |
| 5,868,702 A | 2/1999 | Stevens et al. | |
| 5,888,242 A | 3/1999 | Antaki et al. | |
| 5,911,685 A | 6/1999 | Siess et al. | |
| 5,927,956 A | 7/1999 | Lim et al. | |
| 5,941,813 A | 8/1999 | Sievers et al. | |
| 5,951,263 A | 9/1999 | Taylor et al. | |
| 5,957,941 A | 9/1999 | Ream | |
| 5,993,420 A | 11/1999 | Hyman et al. | |
| 6,007,478 A | 12/1999 | Siess et al. | |
| 6,007,479 A | 12/1999 | Rottenberg et al. | |
| 6,015,272 A | 1/2000 | Antaki et al. | |
| 6,015,434 A | 1/2000 | Yamane | |
| 6,018,208 A | 1/2000 | Maher et al. | |
| 6,053,705 A | 4/2000 | Schoeb et al. | |
| 6,056,719 A | 5/2000 | Mickley | |
| 6,058,593 A | 5/2000 | Siess | |
| 6,059,760 A | 5/2000 | Sandmore et al. | |
| 6,068,610 A | 5/2000 | Ellis et al. | |
| 6,071,093 A | 6/2000 | Hart | |
| 6,083,260 A | 7/2000 | Aboul-Hosn | |
| 6,086,527 A | 7/2000 | Talpade | |
| 6,086,570 A | 7/2000 | Aboul-Hosn et al. | |
| 6,106,494 A | 8/2000 | Saravia et al. | |
| 6,109,895 A | 8/2000 | Ray et al. | |
| 6,113,536 A | 9/2000 | Aboul-Hosn et al. | |
| 6,123,659 A | 9/2000 | Le Blanc et al. | |
| 6,123,725 A | 9/2000 | Aboul-Hosn | |
| 6,132,363 A | 10/2000 | Freed et al. | |
| 6,135,943 A | 10/2000 | Yu et al. | |
| 6,136,025 A | 10/2000 | Barbut et al. | |
| 6,139,487 A | 10/2000 | Siess | |
| 6,152,704 A | 11/2000 | Aboul-Hosn et al. | |
| 6,162,194 A | 12/2000 | Shipp | |
| 6,176,822 B1 | 1/2001 | Nix et al. | |
| 6,176,848 B1 | 1/2001 | Rau et al. | |
| 6,186,665 B1 | 2/2001 | Maher et al. | |
| 6,190,304 B1 | 2/2001 | Downey et al. | |
| 6,190,357 B1 | 2/2001 | Ferrari et al. | |
| 6,200,260 B1 | 3/2001 | Bolling | |
| 6,203,528 B1 | 3/2001 | Deckert et al. | |
| 6,210,133 B1 | 4/2001 | Aboul-Hosn et al. | |
| 6,210,318 B1 | 4/2001 | Lederman | |
| 6,210,397 B1 | 4/2001 | Aboul-Hosn et al. | |
| 6,214,846 B1 | 4/2001 | Elliott | |
| 6,217,541 B1 | 4/2001 | Yu | |
| 6,227,797 B1 | 5/2001 | Watterson et al. | |
| 6,234,960 B1 | 5/2001 | Aboul-Hosn et al. | |
| 6,234,995 B1 | 5/2001 | Peacock, III | |
| 6,245,007 B1 | 6/2001 | Bedingham et al. | |
| 6,245,026 B1 | 6/2001 | Campbell et al. | |
| 6,247,892 B1 | 6/2001 | Kazatchkov et al. | |
| 6,248,091 B1 | 6/2001 | Voelker | |
| 6,254,359 B1 | 7/2001 | Aber | |
| 6,254,564 B1 | 7/2001 | Wilk et al. | |
| 6,287,319 B1 | 9/2001 | Aboul-Hosn et al. | |
| 6,287,336 B1 | 9/2001 | Globerman et al. | |
| 6,295,877 B1 | 10/2001 | Aboul-Hosn et al. | |
| 6,299,635 B1 | 10/2001 | Frantzen | |
| 6,305,962 B1 | 10/2001 | Maher et al. | |
| 6,387,037 B1 | 5/2002 | Bolling et al. | |
| 6,395,026 B1 | 5/2002 | Aboul-Hosn et al. | |
| 6,413,222 B1 | 7/2002 | Pantages et al. | |
| 6,422,990 B1 | 7/2002 | Prem | |

(56) References Cited

U.S. PATENT DOCUMENTS

| | | |
|---|---|---|
| 6,425,007 B1 | 7/2002 | Messinger |
| 6,428,464 B1 | 8/2002 | Bolling |
| 6,454,775 B1 | 9/2002 | Demarais et al. |
| 6,468,298 B1 | 10/2002 | Pelton |
| 6,494,694 B2 | 12/2002 | Lawless et al. |
| 6,503,224 B1 | 1/2003 | Forman et al. |
| 6,508,777 B1 | 1/2003 | Macoviak et al. |
| 6,508,787 B2 | 1/2003 | Erbel Reimund et al. |
| 6,517,315 B2 | 2/2003 | Belady |
| 6,517,528 B1 | 2/2003 | Pantages et al. |
| 6,527,699 B1 | 3/2003 | Goldowsky |
| 6,532,964 B2 | 3/2003 | Aboul-Hosn et al. |
| 6,533,716 B1 | 3/2003 | Schmitz-Rode et al. |
| 6,544,216 B1 | 4/2003 | Sammler et al. |
| 6,547,519 B2 | 4/2003 | Deblanc et al. |
| 6,565,598 B1 | 5/2003 | Lootz |
| 6,572,349 B2 | 6/2003 | Sorensen et al. |
| 6,613,008 B2 | 9/2003 | Aboul-Hosn et al. |
| 6,616,323 B2 | 9/2003 | McGill |
| 6,623,420 B2 | 9/2003 | Reich et al. |
| 6,623,475 B1 | 9/2003 | Siess |
| 6,641,093 B2 | 11/2003 | Coudrais |
| 6,641,558 B1 | 11/2003 | Aboul-Hosn et al. |
| 6,645,241 B1 | 11/2003 | Strecker |
| 6,673,105 B1 | 1/2004 | Chen |
| 6,692,318 B2 | 2/2004 | McBride |
| 6,709,418 B2 | 3/2004 | Aboul-Hosn et al. |
| 6,716,189 B1 | 4/2004 | Jarvik et al. |
| 6,749,598 B1 | 6/2004 | Keren et al. |
| 6,776,578 B2 | 8/2004 | Belady |
| 6,776,794 B1 | 8/2004 | Hong et al. |
| 6,783,328 B2 | 8/2004 | Lucke et al. |
| 6,790,171 B1 | 9/2004 | Gruendeman et al. |
| 6,794,789 B2 | 9/2004 | Siess et al. |
| 6,817,836 B2 | 11/2004 | Nose et al. |
| 6,835,049 B2 | 12/2004 | Ray |
| 6,866,625 B1 | 3/2005 | Ayre et al. |
| 6,866,805 B2 | 3/2005 | Hong et al. |
| 6,887,215 B2 | 5/2005 | McWeeney |
| 6,889,082 B2 | 5/2005 | Bolling et al. |
| 6,926,662 B2 | 8/2005 | Aboul-Hosn et al. |
| 6,935,344 B1 | 8/2005 | Aboul-Hosn et al. |
| 6,949,066 B2 | 9/2005 | Bearnson et al. |
| 6,962,488 B2 | 11/2005 | Davis et al. |
| 6,966,748 B2 | 11/2005 | Woodard et al. |
| 6,972,956 B2 | 12/2005 | Franz et al. |
| 6,974,436 B1 | 12/2005 | Aboul-Hosn et al. |
| 6,981,942 B2 | 1/2006 | Khaw et al. |
| 6,984,392 B2 | 1/2006 | Bechert et al. |
| 7,010,954 B2 | 3/2006 | Siess et al. |
| 7,011,620 B1 | 3/2006 | Siess |
| 7,014,417 B2 | 3/2006 | Salomon |
| 7,018,182 B2 | 3/2006 | O'Mahony et al. |
| 7,022,100 B1 | 4/2006 | Aboul-Hosn et al. |
| 7,122,019 B1 | 10/2006 | Kesten et al. |
| 7,150,711 B2 | 12/2006 | Nusser et al. |
| 7,160,243 B2 | 1/2007 | Medvedev |
| 7,172,551 B2 | 2/2007 | Leasure |
| 7,175,588 B2 | 2/2007 | Morello |
| 7,214,038 B2 | 5/2007 | Saxer et al. |
| 7,238,010 B2 | 7/2007 | Hershberger et al. |
| 7,241,257 B1 | 7/2007 | Ainsworth et al. |
| 7,284,956 B2 | 10/2007 | Nose et al. |
| 7,288,111 B1 | 10/2007 | Holloway et al. |
| 7,290,929 B2 | 11/2007 | Smith et al. |
| 7,329,236 B2 | 2/2008 | Kesten et al. |
| 7,381,179 B2 | 6/2008 | Aboul-Hosn et al. |
| 7,478,999 B2 | 1/2009 | Limoges |
| 7,491,163 B2 | 2/2009 | Viole et al. |
| 7,534,258 B2 | 5/2009 | Gomez et al. |
| 7,633,193 B2 | 12/2009 | Masoudipour et al. |
| 7,682,673 B2 | 3/2010 | Houston et al. |
| 7,722,568 B2 | 5/2010 | Lenker et al. |
| 7,736,296 B2 | 6/2010 | Siess et al. |
| 7,780,628 B1 | 8/2010 | Keren et al. |
| 7,878,967 B1 | 2/2011 | Khanal |
| 7,934,912 B2 | 5/2011 | Voltenburg, Jr. et al. |
| 7,942,844 B2 | 5/2011 | Moberg et al. |
| 7,998,190 B2 | 8/2011 | Gharib et al. |
| 8,025,647 B2 | 9/2011 | Siess et al. |
| 8,052,399 B2 | 11/2011 | Stemple et al. |
| 8,062,008 B2 | 11/2011 | Voltenburg, Jr. et al. |
| 8,114,008 B2 | 2/2012 | Hidaka et al. |
| 8,123,669 B2 | 2/2012 | Siess et al. |
| 8,142,400 B2 | 3/2012 | Rotem et al. |
| 8,206,350 B2 | 6/2012 | Mann et al. |
| 8,216,122 B2 | 7/2012 | Kung et al. |
| 8,236,040 B2 | 8/2012 | Mayberry et al. |
| 8,277,470 B2 | 10/2012 | Demarais et al. |
| 8,317,715 B2 | 11/2012 | Belleville et al. |
| 8,333,687 B2 | 12/2012 | Farnan et al. |
| 8,364,278 B2 | 1/2013 | Pianca et al. |
| 8,608,635 B2 | 12/2013 | Yomtov et al. |
| 8,690,749 B1 | 4/2014 | Nunez |
| 8,721,517 B2 | 5/2014 | Zeng et al. |
| 8,784,441 B2 | 7/2014 | Rosenbluth et al. |
| 8,790,236 B2 | 7/2014 | Larose et al. |
| 8,795,576 B2 | 8/2014 | Tao et al. |
| 8,814,776 B2 | 8/2014 | Hastie et al. |
| 8,944,748 B2 | 2/2015 | Liebing |
| 8,992,406 B2 | 3/2015 | Corbett |
| 9,089,670 B2 | 7/2015 | Scheckel |
| 9,217,442 B2 | 12/2015 | Wiessler et al. |
| 9,314,558 B2 | 4/2016 | Er |
| 9,328,741 B2 | 5/2016 | Liebing |
| 9,358,330 B2 | 6/2016 | Schumacher |
| 2002/0010487 A1 | 1/2002 | Evans et al. |
| 2002/0047435 A1 | 4/2002 | Takahashi et al. |
| 2002/0094287 A1 | 7/2002 | Davis |
| 2002/0107506 A1 | 8/2002 | McGuckin et al. |
| 2002/0111663 A1 | 8/2002 | Dahl et al. |
| 2002/0151761 A1 | 10/2002 | Viole et al. |
| 2003/0018380 A1 | 1/2003 | Craig et al. |
| 2003/0023201 A1 | 1/2003 | Aboul-Hosn et al. |
| 2003/0100816 A1 | 5/2003 | Siess |
| 2003/0135086 A1 | 7/2003 | Khaw et al. |
| 2003/0187322 A1 | 10/2003 | Siess |
| 2003/0205233 A1 | 11/2003 | Aboul-Hosn et al. |
| 2003/0208097 A1 | 11/2003 | Aboul-Hosn et al. |
| 2003/0231959 A1 | 12/2003 | Snider |
| 2004/0010229 A1 | 1/2004 | Houde et al. |
| 2004/0044266 A1 | 3/2004 | Siess et al. |
| 2004/0101406 A1 | 5/2004 | Hoover |
| 2004/0113502 A1 | 6/2004 | Li et al. |
| 2004/0116862 A1 | 6/2004 | Ray |
| 2004/0152944 A1 | 8/2004 | Medvedev et al. |
| 2004/0253129 A1 | 12/2004 | Sorensen et al. |
| 2005/0049696 A1 | 3/2005 | Siess et al. |
| 2005/0085683 A1 | 4/2005 | Bolling et al. |
| 2005/0090883 A1 | 4/2005 | Westlund et al. |
| 2005/0095124 A1 | 5/2005 | Arnold et al. |
| 2005/0113631 A1 | 5/2005 | Bolling et al. |
| 2005/0135942 A1 | 6/2005 | Wood et al. |
| 2005/0137680 A1 | 6/2005 | Ortiz et al. |
| 2005/0165466 A1 | 7/2005 | Morris et al. |
| 2005/0250975 A1 | 11/2005 | Carrier et al. |
| 2005/0277912 A1 | 12/2005 | John |
| 2006/0005886 A1 | 1/2006 | Parrino et al. |
| 2006/0008349 A1 | 1/2006 | Khaw |
| 2006/0036127 A1 | 2/2006 | Delgado, III et al. |
| 2006/0058869 A1 | 3/2006 | Olson et al. |
| 2006/0062672 A1 | 3/2006 | McBride et al. |
| 2006/0063965 A1 | 3/2006 | Aboul-Hosn et al. |
| 2006/0089521 A1 | 4/2006 | Chang |
| 2006/0155158 A1 | 7/2006 | Aboul-Hosn |
| 2006/0167404 A1 | 7/2006 | Pirovano et al. |
| 2007/0142785 A1 | 6/2007 | Lundgaard et al. |
| 2007/0156006 A1 | 7/2007 | Smith et al. |
| 2007/0203442 A1 | 8/2007 | Bechert et al. |
| 2007/0212240 A1 | 9/2007 | Voyeux et al. |
| 2007/0217932 A1 | 9/2007 | Voyeux et al. |
| 2007/0217933 A1 | 9/2007 | Haser et al. |
| 2007/0233270 A1 | 10/2007 | Weber et al. |
| 2007/0237739 A1 | 10/2007 | Doty |

(56) References Cited

U.S. PATENT DOCUMENTS

| | | |
|---|---|---|
| 2007/0248477 A1 | 10/2007 | Nazarifar et al. |
| 2008/0004645 A1 | 1/2008 | To et al. |
| 2008/0004690 A1 | 1/2008 | Robaina |
| 2008/0031953 A1 | 2/2008 | Takakusagi et al. |
| 2008/0103516 A1 | 5/2008 | Wulfman et al. |
| 2008/0103591 A1 | 5/2008 | Siess |
| 2008/0114339 A1 | 5/2008 | McBride et al. |
| 2008/0119943 A1 | 5/2008 | Armstrong et al. |
| 2008/0132748 A1 | 6/2008 | Shifflette |
| 2008/0167679 A1 | 7/2008 | Papp |
| 2008/0306327 A1 | 12/2008 | Shifflette |
| 2009/0018567 A1 | 1/2009 | Escudero et al. |
| 2009/0023975 A1 | 1/2009 | Marseille et al. |
| 2009/0024085 A1 | 1/2009 | To et al. |
| 2009/0053085 A1 | 2/2009 | Thompson et al. |
| 2009/0062597 A1 | 3/2009 | Shifflette |
| 2009/0073037 A1 | 3/2009 | Penna et al. |
| 2009/0087325 A1 | 4/2009 | Voltenburg, Jr. et al. |
| 2009/0093764 A1 | 4/2009 | Pfeffer et al. |
| 2009/0093765 A1 | 4/2009 | Glenn |
| 2009/0093796 A1 | 4/2009 | Pfeffer et al. |
| 2009/0099638 A1 | 4/2009 | Grewe |
| 2009/0112312 A1 | 4/2009 | Larose et al. |
| 2009/0118567 A1 | 5/2009 | Siess |
| 2009/0163864 A1 | 6/2009 | Breznock et al. |
| 2009/0171137 A1 | 7/2009 | Farnan et al. |
| 2009/0182188 A1 | 7/2009 | Marseille et al. |
| 2009/0234378 A1 | 9/2009 | Escudero et al. |
| 2010/0030161 A1 | 2/2010 | Duffy |
| 2010/0030186 A1 | 2/2010 | Stivland |
| 2010/0041939 A1 | 2/2010 | Siess |
| 2010/0047099 A1 | 2/2010 | Miyazaki et al. |
| 2010/0087773 A1 | 4/2010 | Ferrari |
| 2010/0094089 A1 | 4/2010 | Litscher et al. |
| 2010/0127871 A1 | 5/2010 | Pontin |
| 2010/0137802 A1 | 6/2010 | Yodfat et al. |
| 2010/0174239 A1 | 7/2010 | Yodfat et al. |
| 2010/0191035 A1 | 7/2010 | Kang et al. |
| 2010/0197994 A1 | 8/2010 | Mehmanesh |
| 2010/0268017 A1 | 10/2010 | Siess et al. |
| 2010/0274330 A1 | 10/2010 | Burwell et al. |
| 2010/0286210 A1 | 11/2010 | Murata et al. |
| 2010/0286791 A1 | 11/2010 | Goldsmith |
| 2011/0004046 A1 | 1/2011 | Campbell et al. |
| 2011/0004291 A1 | 1/2011 | Davis et al. |
| 2011/0009687 A1 | 1/2011 | Mohl |
| 2011/0015610 A1 | 1/2011 | Plahey et al. |
| 2011/0034874 A1 | 2/2011 | Reitan et al. |
| 2011/0076439 A1 | 3/2011 | Zeilon |
| 2011/0098805 A1 | 4/2011 | Dwork et al. |
| 2011/0106004 A1 | 5/2011 | Eubanks et al. |
| 2011/0152831 A1 | 6/2011 | Rotem et al. |
| 2011/0152906 A1 | 6/2011 | Escudero et al. |
| 2011/0152907 A1 | 6/2011 | Escudero et al. |
| 2011/0218516 A1 | 9/2011 | Grigorov |
| 2011/0237863 A1 | 9/2011 | Ricci et al. |
| 2011/0257462 A1 | 10/2011 | Rodefeld et al. |
| 2011/0270182 A1 | 11/2011 | Breznock et al. |
| 2011/0275884 A1 | 11/2011 | Scheckel |
| 2011/0300010 A1 | 12/2011 | Jarnagin et al. |
| 2012/0059213 A1 | 3/2012 | Spence et al. |
| 2012/0059460 A1 | 3/2012 | Reitan |
| 2012/0083740 A1 | 4/2012 | Chebator et al. |
| 2012/0142994 A1 | 6/2012 | Toellner |
| 2012/0172654 A1 | 7/2012 | Bates |
| 2012/0172655 A1 | 7/2012 | Campbell et al. |
| 2012/0172656 A1 | 7/2012 | Walters et al. |
| 2012/0178985 A1 | 7/2012 | Walters et al. |
| 2012/0178986 A1 | 7/2012 | Campbell et al. |
| 2012/0184803 A1 | 7/2012 | Simon et al. |
| 2012/0220854 A1 | 8/2012 | Messerly et al. |
| 2012/0224970 A1 | 9/2012 | Schumacher et al. |
| 2012/0234411 A1 | 9/2012 | Scheckel et al. |
| 2012/0237357 A1 | 9/2012 | Schumacher et al. |
| 2012/0265002 A1 | 10/2012 | Roehn et al. |
| 2013/0041202 A1 | 2/2013 | Toellner et al. |
| 2013/0053622 A1 | 2/2013 | Corbett |
| 2013/0053623 A1 | 2/2013 | Evans et al. |
| 2013/0085318 A1 | 4/2013 | Toellner et al. |
| 2013/0085319 A1 | 4/2013 | Evans et al. |
| 2013/0096364 A1 | 4/2013 | Reichenbach et al. |
| 2013/0106212 A1 | 5/2013 | Nakazumi et al. |
| 2013/0138205 A1 | 5/2013 | Kushwaha et al. |
| 2013/0204362 A1 | 8/2013 | Toellner et al. |
| 2013/0209292 A1 | 8/2013 | Baykut et al. |
| 2013/0245360 A1 | 9/2013 | Schumacher et al. |
| 2013/0303831 A1 | 11/2013 | Evans et al. |
| 2013/0303969 A1 | 11/2013 | Keenan et al. |
| 2013/0303970 A1 | 11/2013 | Keenan et al. |
| 2013/0331639 A1 | 12/2013 | Campbell et al. |
| 2014/0010686 A1* | 1/2014 | Tanner ............... A61M 1/1036 417/420 |
| 2014/0012065 A1 | 1/2014 | Fitzgerald et al. |
| 2014/0039465 A1 | 2/2014 | Schulz Heike et al. |
| 2014/0051908 A1 | 2/2014 | Khanal et al. |
| 2014/0067057 A1 | 3/2014 | Callaway et al. |
| 2014/0088455 A1 | 3/2014 | Christensen et al. |
| 2014/0163664 A1 | 6/2014 | Goldsmith |
| 2014/0255176 A1 | 9/2014 | Bredenbreuker et al. |
| 2014/0275725 A1 | 9/2014 | Schenck et al. |
| 2014/0275726 A1 | 9/2014 | Zeng |
| 2014/0303596 A1 | 10/2014 | Schumacher et al. |
| 2015/0031936 A1 | 1/2015 | Larose et al. |
| 2015/0051435 A1 | 2/2015 | Siess et al. |
| 2015/0051436 A1 | 2/2015 | Spanier et al. |
| 2015/0080743 A1 | 3/2015 | Siess et al. |
| 2015/0087890 A1 | 3/2015 | Spanier et al. |
| 2015/0141738 A1 | 5/2015 | Toellner et al. |
| 2015/0141739 A1 | 5/2015 | Hsu et al. |
| 2015/0151032 A1 | 6/2015 | Voskoboynikov et al. |
| 2015/0209498 A1 | 7/2015 | Franano et al. |
| 2015/0250935 A1 | 9/2015 | Anderson et al. |
| 2015/0290372 A1 | 10/2015 | Muller et al. |
| 2015/0343179 A1 | 12/2015 | Schumacher et al. |
| 2016/0250399 A1 | 9/2016 | Tiller et al. |
| 2016/0250400 A1 | 9/2016 | Schumacher |
| 2016/0256620 A1 | 9/2016 | Schekel Mario et al. |

FOREIGN PATENT DOCUMENTS

| | | |
|---|---|---|
| EP | 0533432 A1 | 3/1993 |
| EP | 1393762 A1 | 3/2004 |
| EP | 1591079 A1 | 11/2005 |
| EP | 2298374 A1 | 3/2011 |
| FR | 2267800 A1 | 11/1975 |
| GB | 2239675 A | 7/1991 |
| JP | S4823295 U | 3/1973 |
| JP | S58190448 A | 11/1983 |
| JP | H02211169 A | 8/1990 |
| JP | H06114101 A | 4/1994 |
| JP | H08196624 A | 8/1996 |
| JP | H1099447 A | 4/1998 |
| JP | 3208454 B2 | 9/2001 |
| TW | 500877 B2 | 9/2002 |
| WO | 9526695 A2 | 10/1995 |
| WO | 9715228 A1 | 5/1997 |
| WO | 0019097 A1 | 4/2000 |
| WO | 0043062 A1 | 7/2000 |
| WO | 0069489 A1 | 11/2000 |
| WO | 0124867 A1 | 4/2001 |
| WO | 02070039 A2 | 9/2002 |
| WO | 03103745 A2 | 12/2003 |
| WO | 2005089674 A1 | 9/2005 |
| WO | 2005123158 A1 | 12/2005 |
| WO | 2009073037 A1 | 6/2009 |
| WO | 2009076460 A2 | 6/2009 |
| WO | 2010133567 A1 | 11/2010 |
| WO | 2010149393 A1 | 12/2010 |
| WO | 2011035926 A1 | 3/2011 |
| WO | 2011035929 A2 | 3/2011 |
| WO | 2011039091 A1 | 4/2011 |
| WO | 2011076439 A1 | 6/2011 |
| WO | 2011089022 A1 | 7/2011 |
| WO | 2012007140 A1 | 1/2012 |

(56) References Cited

FOREIGN PATENT DOCUMENTS

| WO | 2012007141 A1 | 1/2012 |
|---|---|---|
| WO | 2013148697 A1 | 10/2013 |
| WO | 2013160407 A1 | 10/2013 |
| WO | 2014019274 A1 | 2/2014 |
| WO | 2015063277 A2 | 5/2015 |

OTHER PUBLICATIONS

Abiomed—Recovering Hearts. Saving Lives., Impella 2.5 System, Instructions for Use, Jul. 2007, in 86 sheets.
Aboul-Hosn et al., "The Hemopump: Clinical Results and Future Applications", Assisted Circulation 4, 1995, in 14 pages.
Barras et al., "Nitinol—Its Use in Vascular Surgery and Other Applications," Eur. J. Vasc. Endovasc. Surg., 2000, pp. 564-569; vol. 19.
Biscarini et al., "Enhanced Nitinol Properties for Biomedical Applications," Recent Patents on Biomedical Engineering, 2008, pp. 180-196, vol. 1(3).
Cardiovascular Diseases (CVDs) Fact Sheet No. 317; World Health Organization [Online], Sep. 2011. http://www.who.int/mediacentre/factsheets/fs317/en/index.html, accessed on Aug. 29, 2012.
Compendium of Technical and Scientific Information for the HEMOPUMP Temporary Cardiac Assist System, Johnson & Johnson Interventional Systems, 1988, in 15 pages.
Dekker et al., "Efficacy of a New Intraaortic Propeller Pump vs the Intraaortic Balloon Pump*, An Animal Study", Chest, Jun. 2003, vol. 123, No. 6, pp. 2089-2095.
Duerig et al., "An Overview of Nitinol Medical Applications," Materials Science Engineering, 1999, pp. 149-160; vol. A273.
European Search Report received in European Patent Application No. 05799883.3, dated May 10, 2011, in 4 pages.
Extended European Search Report received in European Patent Application No. 07753903.9, dated Oct. 8, 2012, in 7 pages.
Extended European Search Report received in European Patent Application No. 13790890.1, dated Jan. 7, 2016, in 6 pages.
Extended European Search Report received in European Patent Application No. 13791118.6, dated Jan. 7, 2016, in 6 pages.
Extended European Search Report received in European Patent Application No. 13813687.4, dated Feb. 24, 2016, in 6 pages.
Extended European Search Report received in European Patent Application No. 13813867.2, dated Feb. 26, 2016, in 7 pages.
Extended European Search Report received in European Patent Application No. 14779928.2, dated Oct. 7, 2016, in 7 pages.
Extended European Search Report received in European Patent Application No. 14764392.8, dated Oct. 27, 2016, in 7 pages.
Federal and Drug Administration 510(k) Summary for Predicate Device IMPELLA 2.5 (K112892), prepared Sep. 5, 2012.
Grech, "Percutaneous Coronary Intervention. I: History and Development," BMJ., May 17, 2003, pp. 1080-1082, vol. 326.
Hsu et al., "Review of Recent Patents on Foldable Ventricular Assist Devices," Recent Patents on Biomedical Engineering, 2012, pp. 208-222, vol. 5.
Ide et al., "Evaluation of the Pulsatility of a New Pulsatile Left Ventricular Assist Device—the Integrated Cardioassist Catheter-in Dogs," J. of Thorac and Cardiovasc Sur, Feb. 1994, pp. 569-0575, vol. 107(2).
Ide et al., "Hemodynamic Evaluation of a New Left Ventricular Assist Device: An Integrated Cardioassist Catheter as a Julsatile Left Ventricle-Femoral Artery Bypass," Blackwell Scientific Publications, Inc., 1992, pp. 286-290, vol. 16(3).
Impella CP®—Instructions for Use & Clinical Reference Manual (United States only), Abiomed, Inc., Jul. 2014, 148 pages, www.abiomed.com.
Impella LD® with the Impella®Controller—Circulatory Support System—Instructions for Use & Clinical Reference Manual (United States only), Abiomed, Inc., Sep. 2010, 132 pages, www.abiomed.com.
International Preliminary Examination Report received in International Patent Application No. PCT/US2003/04853, dated Jul. 26, 2004, in 5 pages.
International Preliminary Examination Report received in International Patent Application No. PCT/US2003/04401, dated May 18, 2004, in 4 pages.
International Preliminary Report on Patentability and Written Opinion of the International Searching Authority received in International Patent Application No. PCT/US2005/033416, dated Mar. 20, 2007, in 7 pages.
International Preliminary Report on Patentability and Written Opinion of the International Searching Authority received in International Patent Application No. PCT/US2007/007313, dated Sep. 23, 2008, in 6 pages.
International Preliminary Report on Patentability and Written Opinion received in International Patent Application No. PCT/US2014/020878, dated Sep. 15, 2015, in 8 pages.
International Search Report and Written Opinion received in International Patent Application No. PCT/US2005/033416, dated Dec. 11, 2006, in 8 pages.
International Search Report and Written Opinion received in International Patent Application No. PCT/US2007/007313, dated Mar. 4, 2008, in 6 pages.
International Search Report and Written Opinion received in International Patent Application No. PCT/US2012/020382, dated Jul. 31, 2012, in 11 pages.
nternational Search Report and Written Opinion received in International Patent Application No. PCT/US2012/020369, dated Jul. 30, 2012, in 10 pages.
International Search Report and Written Opinion received in International Patent Application No. PCT/US2012/020553, dated Aug. 17, 2012, in 8 pages.
International Search Report and Written Opinion received in International Patent Application No. PCT/US2012/020383, dated Aug. 17, 2012; in 9 pages.
International Search Report and Written Opinion received in International Patent Application No. PCT/US2013/040798, dated Aug. 21, 2013, in 16 pages.
International Search Report and Written Opinion received in International Patent Application No. PCT/US2013/040799, dated Aug. 21, 2013, in 19 pages.
International Search Report and Written Opinion received in International Patent Application No. PCT/US2013/040809, dated Sep. 2, 2013, in 25 pages.
International Search Report and Written Opinion received in International Patent Application No. PCT/US2013/048332, dated Oct. 16, 2013, in 14 pages.
International Search Report and Written Opinion received in International Patent Application No. PCT/US2013/048343, dated Oct. 11, 2013, in 15 pages.
International Search Report and Written Opinion received in International Patent Application No. PCT/US2014/020878, dated May 7, 2014, in 11 pages.
International Search Report and Written Opinion received in International Patent Application No. PCT/US2015/026013, dated Oct. 22, 2015, in 8 pages.
International Search Report and Written Opinion received in International Patent Application No. PCT/US2015/026014, dated Oct. 22, 2015, in 8 pages.
International Search Report and Written Opinion received in International Patent Application No. PCT/US2015/026025, dated Oct. 22, 2015, in 12 pages.
International Search Report and Written Opinion received in International Patent Application No. PCT/US2015/025959, dated Oct. 22, 2015, in 9 pages.
International Search Report and Written Opinion received in International Patent Application No. PCT/US2015/025960, dated Oct. 22, 2015, in 11 pages.
International Search Report and Written Opinion received in International Patent Application No. PCT/US2015/045370, dated Feb. 25, 2016, in 10 pages.

(56) References Cited

OTHER PUBLICATIONS

International Search Report and Written Opinion received in International Patent Application No. PCT/US2016/014371, dated Jul. 28, 2016, in 16 pages.
International Search Report and Written Opinion received in International Patent Application No. PCT/US2016/014379, dated Jul. 29, 2016, in 17 pages.
International Search Report and Written Opinion received in International Patent Application No. PCT/US2016/014391, dated Jul. 28, 2016, in 15 pages.
International Search Report received in International Patent Application No. PCT/US2003/004401, dated Jan. 22, 2004, in 7 pages.
International Search Report received in International Patent Application No. PCT/US2003/004853, dated Nov. 10, 2003, in 5 pages.
International Search Report and Written Opinion received in International Patent Application No. PCT/US2010/040847, dated Jan. 6, 2011, in 15 pages.
International Search Report and Written Opinion received in International Patent Application No. PCT/US2014/020790, dated Oct. 9, 2014, in 9 pages.
International Search Report and Written Opinion received in International Patent Application No. PCT/US2016/051553, dated Mar. 23, 2017, in 11 pages.
JOMED Reitan Catheter Pump RCP, Percutaneous Circulatory Support, in 10 pages, believed to be published prior to Oct. 15, 2003.
JOMED Reitan Catheter Pump RCP, Feb. 18, 2003, in 4 pages.
Krishnamani et al., "Emerging Ventricular Assist Devices for Long-Term Cardiac Support," National Review, Cardiology, Feb. 2010, pp. 71-76, vol. 7.
Kunst et al., "Integrated unit for programmable control of the 21F Hemopump and registration of physiological signals," Medical & Biological Engineering & Computing, Nov. 1994, pp. 694-696.
Mihaylov et al., "Development of a New Introduction Technique for the Pulsatile Catheter Pump," Artificial Organs, 1997, pp. 425-427; vol. 21(5).
Mihaylov et al., "Evaluation of the Optimal Driving Mode During Left Ventricular Assist with Pulsatile Catheter Pump in Calves," Artificial Organs, 1999, pp. 1117-1122; vol. 23(12).
Minimally Invasive Cardiac Assist JOMED Catheter PumpTM, in 6 pages, believed to be published prior to Jun. 16, 1999.
Morgan, "Medical Shape Memory Alloy Applications—The Market and its Products," Materials Science and Engineering, 2004, pp. 16-23, vol. A 378.
Morsink et al., "Numerical Modelling of Blood Flow Behaviour in the Valved Catheter of the PUCA-Pump, a LVAD," The International Journal of Artificial Organs, 1997, pp. 277-284; vol. 20(5).
Nishimura et al, "The Enabler Cannula Pump: A Novel Circulatory Support System," The International Journal of Artificial Organs, 1999, pp. 317-323; vol. 22(5).
Nullity Action against the owner of the German part DE 50 2007 005 015.6 of European patent EP 2 047 872 B1, dated Jul. 13, 2015, in 61 pages.
Petrini et al., "Biomedical Applications of Shape Memory Alloys," Journal of Metallurgy, 2011, pp. 1-15.
Raess et al., "Impella 2.5," J. Cardiovasc. Transl. Res., 2009, pp. 168-172, vol. 2(2).
Rakhorst et al., "In Vitro Evaluation of the Influence of Pulsatile Intraventricular Pumping on Ventricular Pressure Patterns," Artificial Organs, 1994, pp. 494-499, vol. 18(7).
Reitan, Evaluation of a New Percutaneous Cardiac Assist Device, Department of Cardiology, Faculty of Medicine, Lund University, Sweden, 2002, in 172 pages.
Reitan et al., "Hemodynamic Effects of a New Percutaneous Circulatory Support Device in a Left Ventricular Failure Model," ASAIO Journal, 2003, pp. 731-736, vol. 49.
Reitan et al., "Hydrodynamic Properties of a New Percutaneous Intra-Aortic Axial Flow Pump," ASAIO Journal 2000, pp. 323-328.
Rothman, "The Reitan Catheter Pump: A New Versatile Approach for Hemodynamic Support", London Chest Hospital Barts & The London NHS Trust, Oct. 22-27, 2006 (TCT 2006: Transcatheter Cardiovascular Therapeutics 18th Annual Scientific Symposium, Final Program), in 48 pages.
Schmitz-Rode et al., "An Expandable Percutaneous Catheter Pump for Left Ventricular Support," Journal of the American College of Cardiology, 2005, pp. 1856-1861, vol. 45(11).
Shabari et al., "Improved Hemodynamics with a Novel Miniaturized Intra-Aortic Axial Flow Pump in a Porcine Model of Acute Left Ventricular Dysfunction," ASAIO Journal, 2013, pp. 240-245; vol. 59.
Sharony et al, "Cardiopulmonary Support and Physiology—The Intra-Aortic Cannula Pump: A Novel Assist Device for the Acutely Failing Heart," The Journal of Thoracic and Cardiovascular Surgery, Nov. 1992, pp. 924-929, vol. 118(5).
Sharony et al., "Right Heart Support During Off-Pump Coronary Artery Surgery—A Multi-Center Study," The Heart Surgery Forum, 2002, pp. 13-16, vol. 5(1).
Sieß et al., "Hydraulic refinement of an intraarterial microaxial blood pump", The International Journal of Artificial Organs, 1995, vol. 18, No. 5, pp. 273-285.
Sieß, "Systemanalyse and Entwicklung intravasaler Rotationspumpen zur Herzunterstützung", Helmholtz-Institut fur Blomedixinische Technik an der RWTH Aachen, Jun. 24, 1998, in 105 pages.
Siess et al., "System analysis and development of intravascular rotation pumps for cardiac assist," Dissertation, Shaker Verlag, Aachen, 1999, 39 pages.
Siess et al., "Basic design criteria for rotary blood pumps," H. Masuda, Rotary Blood Pumps, Springer, Japan, 2000, pp. 69-83.
Siess et al., "Concept, realization, and first in vitro testing of an intraarterial microaxial blood pump," Artificial Organs, 1995, pp. 644-652, vol. 19, No. 7, Blackwell Science, Inc., Boston, International Society for Artificial Organs.
Siess et al., "From a lab type to a product: A retrospective view on Impella's assist technology," Artificial Organs, 2001, pp. 414-421, vol. 25, No. 5, Blackwell Science, Inc., International Society for Artificial Organs.
Smith et al., "First-In-Man Study of the Reitan Catheter Pump for Circulatory Support in Patients Undergoing High-Risk Percutaneous Coronary Intervention," Catheterization and Cardiovascular Interventions, 2009, pp. 859-865, vol. 73(7).
Sokolowski et al., "Medical Applications of Shape Memory Polymers," Biomed. Mater. 2007, pp. S23-S27, vol. 2.
"Statistical Analysis and Clinical Experience with the Recover® Pump Systems", Impella CardioSystems GmbH, Sep. 2005, 2 sheets.
Stoeckel et al., "Self-Expanding Nitinol Stents—Material and Design Considerations," European Radiology, 2003, in 13 sheets.
Stolinski et al., "The heart-pump interaction: effects of a microaxial blood pump," International Journal of Artificial Organs, 2002, pp. 1082-1088, vol. 25, Issue 11.
Supplemental European Search Report received from the European Patent Office in EP Application No. EP 05799883 dated Mar. 19, 2010, 3 pages.
Takagaki et al., "A Novel Miniature Ventricular Assist Device for Hemodynamic Support," ASAIO Journal, 2001, pp. 412-416; vol. 47.
Throckmorton et al., "Flexible Impeller Blades in an Axial Flow Pump for Intravascular Cavopulmonary Assistance of the Fontan Physiology," Cardiovascular Engineering and Technology, Dec. 2010, pp. 244-255, vol. 1(4).
Throckmorton et al., "Uniquely shaped cardiovascular stents enhance the pressure generation of intravascular blood pumps," The Journal of Thoracic and Cardiovascular Surgery, Sep. 2012, pp. 704-709, vol. 133, No. 3.
Verkerke et al., "The PUCA Pump: A Left Ventricular Assist Device," Artificial Organs, 1993, pp. 365-368, vol. 17(5).
Verkerke et al., "Numerical Simulation of the PUCA Pump, A Left Ventricular Assist Device," Abstracts of the XIXth ESAO Congress, The International Journal of Artificial Organs, 1992, p. 543, vol. 15(9).
Verkerke et al., "Numerical Simulation of the Pulsating Catheter Pump: A Left Ventricular Assist Device," Artificial Organs, 1999, pp. 924-931, vol. 23(10).

(56) References Cited

OTHER PUBLICATIONS

Wampler et al., "The Stemotomy Hemopump, A Second Generation Intraarterial Ventricular Assist Device," ASAIO Journal, 1993, pp. M218-M223, vol. 39.
Weber et al., "Principles of Impella Cardiac Support," Supplemental to Cardiac Interventions Today, Aug./Sep. 2009.
Written Opinion received in International Patent Application No. PCT/US2003/04853, dated Feb. 25, 2004, 5 pages.
Extended EP Search Report, dated Mar. 15, 2018, for related EP patent application No. EP 15833166.0, in 7 pages.

* cited by examiner

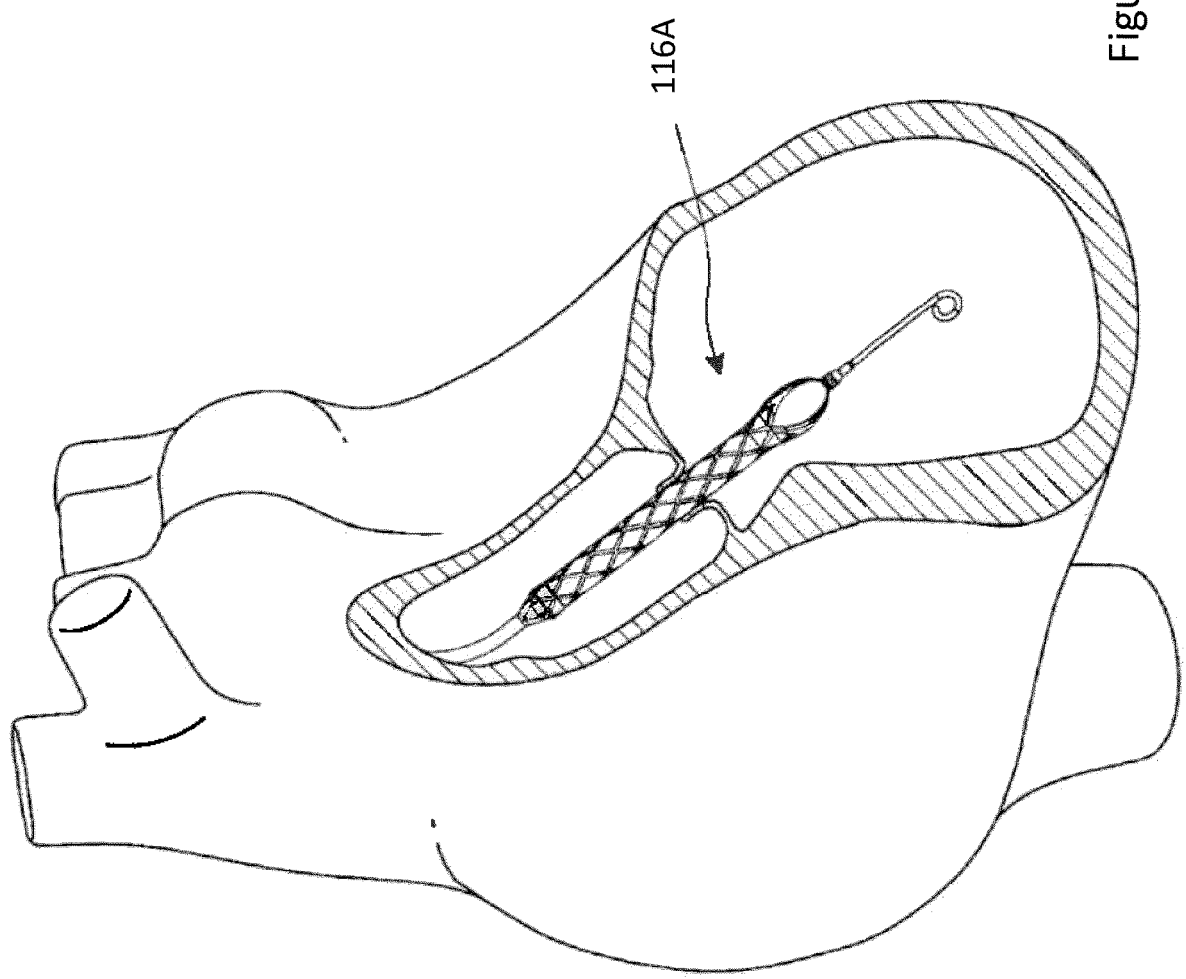

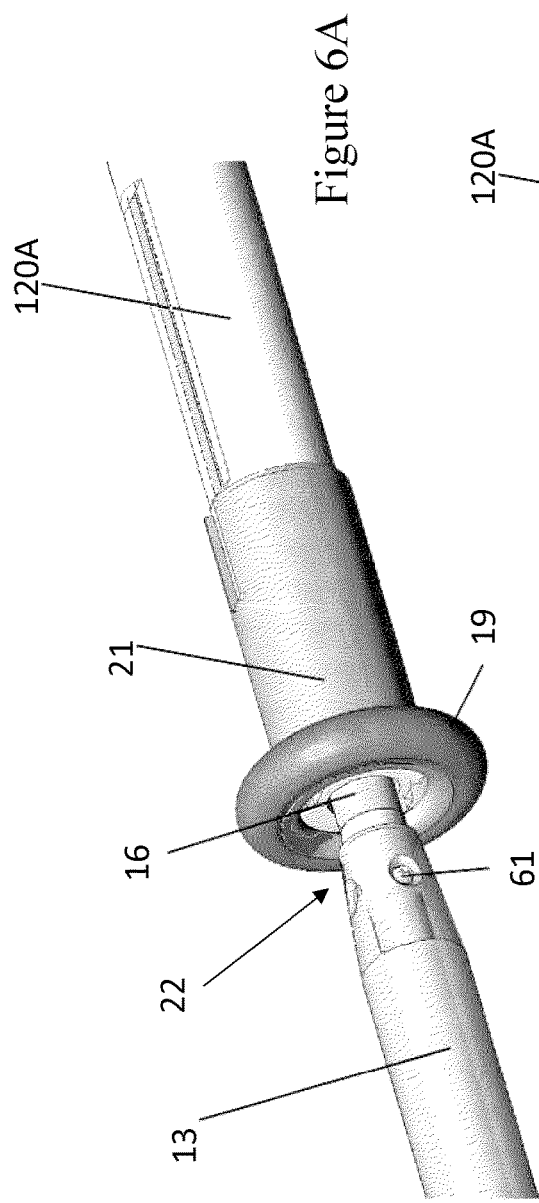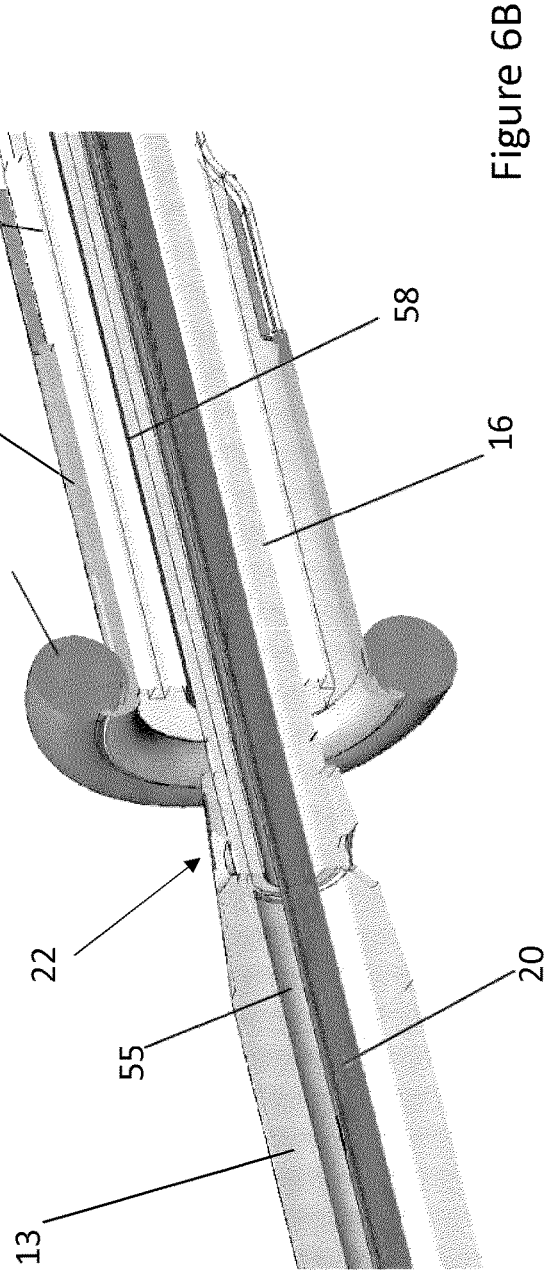

REDUCED ROTATIONAL MASS MOTOR ASSEMBLY FOR CATHETER PUMP

CROSS-REFERENCE TO RELATED APPLICATION

This application is a continuation of U.S. patent application Ser. No. 15/003,576, filed on Jan. 21, 2016, which claims priority to U.S. Provisional Patent Application No. 62/106,670, filed on Jan. 22, 2015, the entire contents of each of which are incorporated by reference herein in their entirety and for all purposes.

BACKGROUND OF THE INVENTION

Field of the Invention

This application is directed to catheter pumps for mechanical circulatory support of a heart.

Description of the Related Art

Heart disease is a major health problem that has high mortality rate. Physicians increasingly use mechanical circulatory support systems for treating heart failure. The treatment of acute heart failure requires a device that can provide support to the patient quickly. Physicians desire treatment options that can be deployed quickly and minimally-invasively.

Mechanical circulatory support (MCS) systems and ventricular assist devices (VADs) have gained greater acceptance for the treatment of acute heart failure, such as to stabilize a patient after cardiogenic shock, during treatment of acute myocardial infarction (MI) or decompensated heart failure, or to support a patient during high risk percutaneous coronary intervention (PCI). An example of an MCS system is a rotary blood pump placed percutaneously, e.g., via a catheter without a surgical cutdown.

In a conventional approach, a blood pump is inserted into the body and connected to the cardiovascular system, for example, to the left ventricle and the ascending aorta to assist the pumping function of the heart. Other known applications include pumping venous blood from the right ventricle to the pulmonary artery for support of the right side of the heart. Typically, acute circulatory support devices are used to reduce the load on the heart muscle for a period of time, to stabilize the patient prior to heart transplant or for continuing support.

There is a need for improved mechanical circulatory support devices for treating acute heart failure. There is a need for devices designed to provide near full heart flow rate and inserted percutaneously (e.g., through the femoral artery without a cutdown).

There is a need for a pump with improved performance and clinical outcomes. There is a need for a pump that can provide elevated flow rates with reduced risk of hemolysis and thrombosis. There is a need for a pump that can be inserted minimally-invasively and provide sufficient flow rates for various indications while reducing the risk of major adverse events.

In one aspect, there is a need for a heart pump that can be placed minimally-invasively, for example, through a 15FR or 12FR incision. In one aspect, there is a need for a heart pump that can provide an average flow rate of 4 Lpm or more during operation, for example, at 62 mmHg of head pressure.

While the flow rate of a rotary pump can be increased by rotating the impeller faster, higher rotational speeds are known to increase the risk of hemolysis, which can lead to adverse outcomes and in some cases death. Higher speeds also lead to performance and patient comfort challenges. Many percutaneous ventricular assist devices (VADs) have driveshafts between the motor and impeller rotating at high speeds. Some percutaneous VADs are designed to rotate at speeds of more than 15,000 RPM, and in some case more than 25,000 RPM in operation. The vibration, noise, and heat from the motor and driveshaft can cause discomfort to the patient when positioned, especially when positioned inside the body. Accordingly, there is a need to for a device that improves performance and patient comfort with a high speed motor.

There is a need for a motor configured to drive an operative device, e.g., a impeller, at a distal portion of the pump. It can be important for the motor to be configured to allow for percutaneous insertion of the pump's impeller.

These and other problems are overcome by the inventions described herein.

SUMMARY OF THE INVENTION

There is an urgent need for a pumping device that can be inserted percutaneously and also provide full cardiac rate flows of the left, right, or both the left and right sides of the heart when called for.

In one embodiment, a catheter pump system is disclosed. The catheter pump system can include an impeller and a catheter body having a lumen in which fluid flows proximally therethrough during operation of the catheter pump. The catheter pump system can include a drive shaft disposed inside the catheter body and coupled with the impeller at a distal portion of the drive shaft, the drive shaft configured such that rotation of the drive shaft causes the impeller to rotate. The catheter pump system can include a motor assembly. The motor assembly can include a chamber, at least a portion of the chamber in fluid communication with the lumen of the catheter body. The motor assembly can also include a rotor disposed in the at least a portion of the chamber, the rotor mechanically coupled with a proximal portion of the drive shaft such that rotation of the rotor causes the drive shaft to rotate. The motor assembly can include a stator assembly disposed about the rotor and configured to cause the rotor to rotate. No cooling fins extend outside an exterior surface of the motor assembly.

In another embodiment, a catheter pump system is disclosed. The catheter pump system can include an impeller and a catheter body having a lumen therethrough, the impeller mechanically coupled with a distal portion of the catheter body. The catheter pump system can include a guidewire guide tube disposed through the lumen from a proximal portion of the catheter pump to a distal portion of the catheter pump, the guidewire guide tube configured to receive a guidewire therein. The catheter pump system can include an end cap secured to a proximal end portion of the guide tube, the end cap configured such that axial movement of the end cap relative to the catheter body causes the guidewire guide tube to be removed from the catheter pump. The catheter pump system can include a resealable closure device disposed at a proximal portion of the catheter pump, the closure device configured such that when the guidewire guide tube is removed from the catheter pump, the closure device encloses the proximal portion of the catheter pump system.

In another embodiment, a catheter pump system is disclosed. The catheter pump system can include a pump including an impeller for pumping blood. The catheter pump system can include a motor assembly for imparting rotation on the impeller through a drive shaft. The motor assembly can comprise a stator carrying electrical windings and a rotor disposed in at least a portion of the stator, the rotor mechanically coupled with a proximal portion of the drive shaft. The catheter pump system can include a fluid supply system for delivering fluid to the pump during operation of the pump and returning at least some of the supplied fluid to a waste reservoir. The fluid supply system can comprise a fluid channel extending within the stator and a fluid pathway which passes outside the stator. During operation of the pump, at least a first portion of the returning fluid can pass through the fluid channel and at least a second portion of the returning fluid can pass through the fluid pathway.

In another embodiment, a method of operating a pump is disclosed. The pump can comprise a motor which includes a stator assembly having windings and a rotor positioned within the stator assembly. The method can include rotating the rotor by selectively energizing the windings. The method can include cooling the motor by flowing a first fluid portion between the stator assembly and the rotor and by flowing a second fluid portion outside the stator.

BRIEF DESCRIPTION OF THE DRAWINGS

A more complete appreciation of the subject matter of this application and the various advantages thereof can be realized by reference to the following detailed description, in which reference is made to the accompanying drawings in which:

FIG. 1A illustrates one embodiment of a catheter pump system with an impeller assembly configured for percutaneous application and operation.

FIG. 6A is a schematic perspective view of an interface between an output shaft of the motor assembly and a drive shaft of the catheter pump system.

FIG. 6B is a cross-sectional perspective view, taken through the longitudinal axis of the catheter, showing the interface shown in FIG. 6A.

More detailed descriptions of various embodiments of components for heart pumps useful to treat patients experiencing cardiac stress, including acute heart failure, are set forth below.

DETAILED DESCRIPTION

This application is generally directed to apparatuses for inducing motion of a fluid relative to the apparatus. Exemplars of circulatory support systems for treating heart failure, and in particular emergent and/or acute heart failure, are disclosed in U.S. Pat. Nos. 4,625,712; 4,686,982; 4,747,406; 4,895,557; 4,944,722; 6,176,848; 6,926,662; 7,022,100; 7,393,181; 7,841,976; 8,157,719; 8,489,190; 8,597,170; 8,721,517 and U.S. Pub. Nos. 2012/0178986 and 2014/0010686, the entire contents of which patents and publications are incorporated by reference for all purposes. In addition, this application incorporates by reference in its entirety and for all purposes the subject matter disclosed in each of the following concurrently filed applications and the provisional applications to which they claim priority: application Ser. No. 15/003,682, now issued U.S. Pat. No. 9,675,739, entitled "MOTOR ASSEMBLY WITH HEAT EXCHANGER FOR CATHETER PUMP," filed on the same date as this application and claiming priority to U.S. Provisional Patent Application No. 62/106,675; and application Ser. No. 15/003,696, now issued U.S. Pat. No. 9,675,738, entitled "ATTACHMENT MECHANISMS FOR MOTOR OF CATHETER PUMP," filed on the same date as this application and claiming priority to U.S. Provisional Patent Application No. 62/106,673.

In one example, an impeller can be coupled at a distal portion of the apparatus. Some embodiments generally relate to various configurations for a motor assembly adapted to drive an impeller at a distal end of a catheter pump, e.g., a percutaneous heart pump. In such applications, the disclosed motor assembly is disposed outside the patient in some embodiments. In other embodiments, the disclosed motor assembly and/or features of the motor are miniaturized and sized to be inserted within the body, e.g., within the vasculature.

Figure 1B:
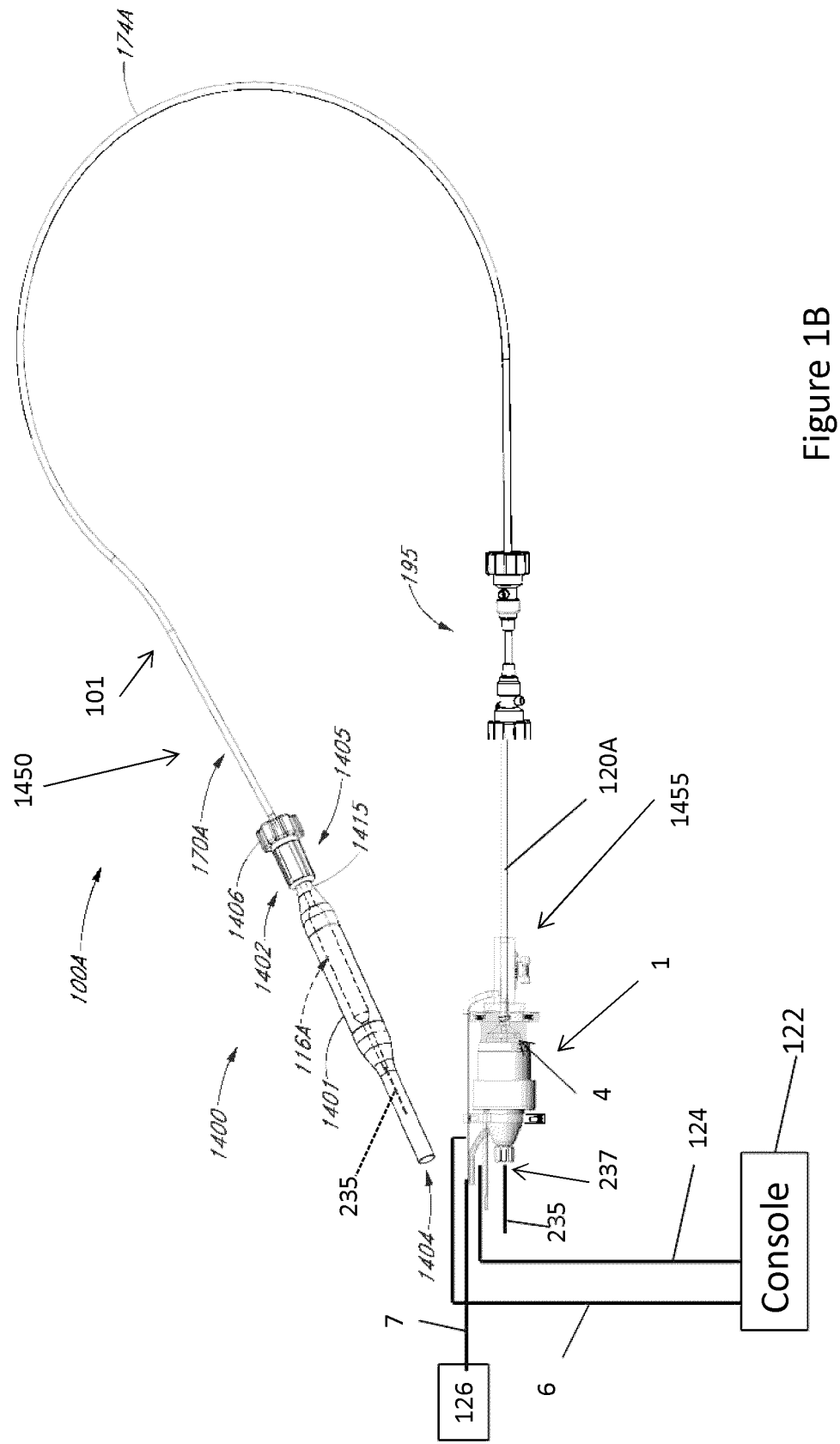
FIG. 1B is a schematic view of one embodiment of a catheter pump system adapted to be used in the manner illustrated in FIG. 1A.

FIGS. 1A-1B show aspects of an exemplary catheter pump 100A that can provide high performance, e.g., high blood flow rates. As shown in FIG. 1B, the pump 100A includes a motor assembly 1 driven by a console 122, which can include an electronic controller and various fluid handling systems. The console 122 directs the operation of the motor 1 and an infusion system that supplies a flow of fluid in the pump 100A. Additional details regarding the console 122 may be found throughout U.S. Patent Publication No. US 2014/0275725, the contents of which are incorporated by reference herein in their entirety and for all purposes.

The pump 100A includes a catheter assembly 101 that can be coupled with the motor assembly 1 and can house an impeller in an impeller assembly 116A within a distal portion of the catheter assembly 101 of the pump 100A. In various embodiments, the impeller is rotated remotely by the motor 1 when the pump 100A is operating. For example, the motor 1 can be disposed outside the patient. In some embodiments, the motor 1 is separate from the console 122, e.g., to be placed closer to the patient. In the exemplary system the pump is placed in the patient in a sterile environment and the console is outside the sterile environment. In one embodiment, the motor is disposed on the sterile side of the system. In other embodiments, the motor 1 is part of the console 122.

Figure 1C:
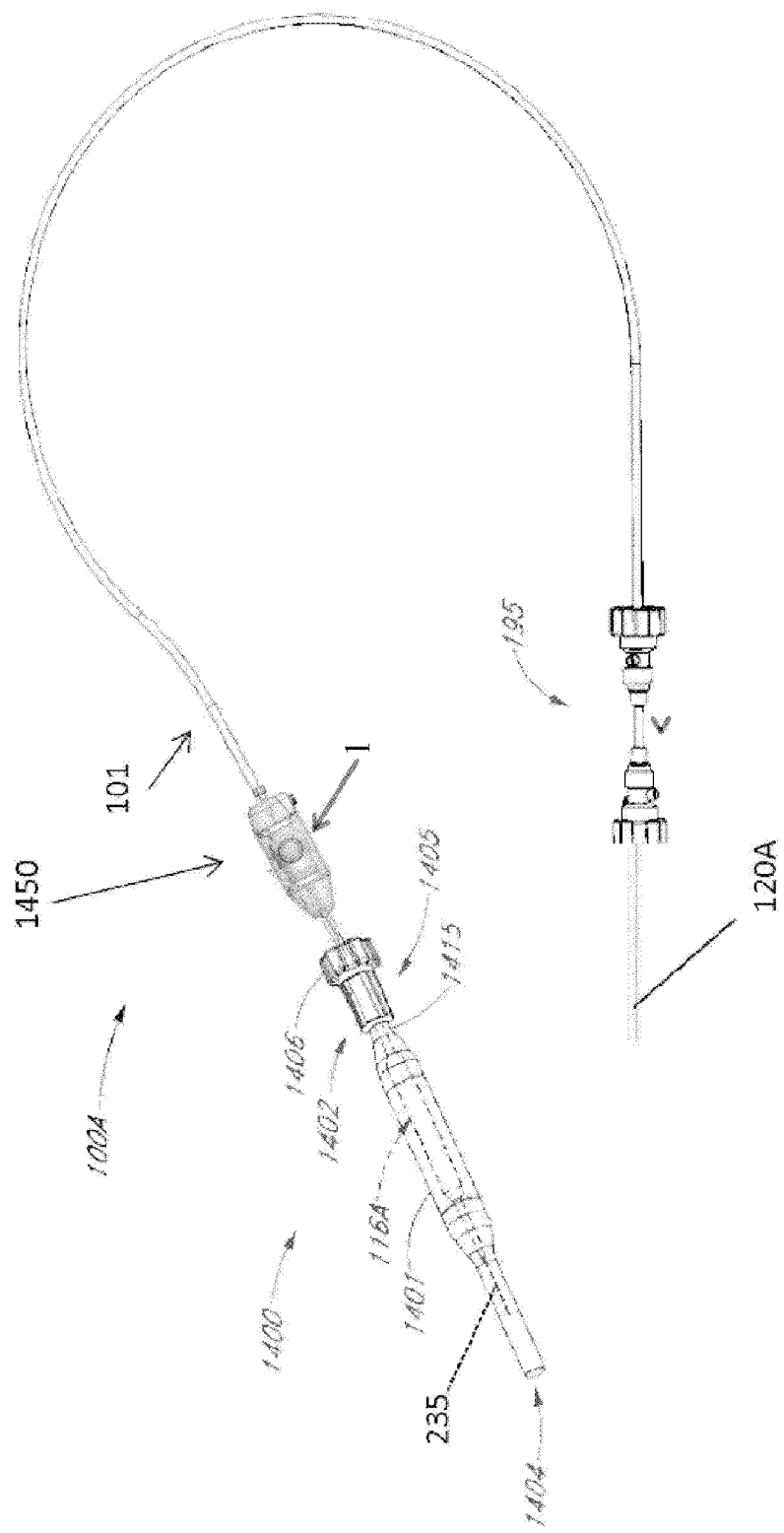
FIG. 1C is a schematic view of another embodiment of a catheter pump system.

In still other embodiments, the motor 1 is miniaturized to be insertable into the patient. For example, FIG. 1C is a schematic view of another embodiment of a catheter pump system. FIG. 1C is similar to FIG. 1B, except the motor 1 is miniaturized for insertion into the body. As shown in FIG. 1C, for example, the motor 1 can be disposed proximal the impeller assembly 116A. The motor 1 can be generally similar to the motor assembly shown in FIG. 2, except the motor 1 is sized and shaped to be inserted into the patient's vasculature. One or more electrical lines may extend from the motor to the console outside the patient. The electrical lines can send signals for controlling the operation of the motor. Such embodiments allow a drive shaft coupled with the impeller and disposed within the catheter assembly 101 to be much shorter, e.g., shorter than the distance from the aortic valve to the aortic arch (about 5 cm or less). Some examples of miniaturized motor catheter pumps and related components and methods are discussed in U.S. Pat. Nos. 5,964,694; 6,007,478; 6,178,922; and 6,176,848, all of which are hereby incorporated by reference herein in their entirety for all purposes. Various embodiments of the motor assembly 1 are disclosed herein, including embodiments having a rotor disposed within a stator assembly. In various embodiments, waste fluid can pass through a housing in which the rotor is disposed to help cool the motor assembly 1.

FIG. 1A illustrates one use of the catheter pump 100A. A distal portion of the pump 100A including a catheter assembly including the impeller assembly 116A is placed in the left ventricle LV of the heart to pump blood from the LV into the aorta. The pump 100A can be used in this way to treat a wide range of heart failure patient populations including, but not limited to, cardiogenic shock (such as acute myocardial infarction, acute decompensated heart failure, and postcardiotomy), myocarditis, and others. The pump can also be used for various other indications including to support a patient during a cardiac invention such as as a high-risk percutaneous coronary intervention (PCI) or VF ablation. One convenient manner of placement of the distal portion of the pump 100A in the heart is by percutaneous access and delivery using a modified Seldinger technique or other methods familiar to cardiologists. These approaches enable the pump 100A to be used in emergency medicine, a catheter lab and in other medical settings. Modifications can also enable the pump 100A to support the right side of the heart. Example modifications that could be used for right side support include providing delivery features and/or shaping a distal portion that is to be placed through at least one heart valve from the venous side, such as is discussed in U.S. Pat. Nos. 6,544,216; 7,070,555; and US 2012-0203056A1, all of which are hereby incorporated by reference herein in their entirety for all purposes.

The impeller assembly 116A can be expandable and collapsible. In the collapsed state, the distal end of the catheter pump 100A can be advanced to the heart, for example, through an artery. In the expanded state the impeller assembly 116A is able to pump blood at relatively high flow rates. In particular, the expandable cannula and impeller configuration allows for decoupling of the insertion size and flow rate, in other words, it allows for higher flow rates than would be possible through a lumen limited to the insertion size with all other things being equal. In FIGS. 1A and 1B, the impeller assembly 116A is illustrated in the expanded state. The collapsed state can be provided by advancing a distal end 170A of an elongate body 174A distally over the impeller assembly 116A to cause the impeller assembly 116A to collapse. This provides an outer profile throughout the catheter assembly and catheter pump 100A that is of small diameter during insertion, for example, to a catheter size of about 12.5 FR in various arrangements. In other embodiments, the impeller assembly 116A is not expandable.

The mechanical components rotatably supporting the impeller within the impeller assembly 116A permit relatively high rotational speeds while controlling heat and particle generation that can come with high speeds. The infusion system delivers a cooling and lubricating solution to the distal portion of the catheter pump 100A for these purposes. The space for delivery of this fluid is extremely limited. Some of the space is also used for return of the fluid as waste fluid. Providing secure connection and reliable routing of fluid into and out of the catheter pump 100A is critical and challenging in view of the small profile of the catheter assembly 101.

When activated, the catheter pump 100A can effectively support, restore and/or increase the flow of blood out of the heart and through the patient's vascular system. In various embodiments disclosed herein, the pump 100A can be configured to produce a maximum flow rate (e.g. low mm Hg) of greater than 4 Lpm, greater than 4.5 Lpm, greater than 5 Lpm, greater than 5.5 Lpm, greater than 6 Lpm, greater than 6.5 Lpm, greater than 7 Lpm, greater than 7.5 Lpm, greater than 8 Lpm, greater than 9 Lpm, or greater than 10 Lpm. In various embodiments, the pump 100A can be configured to produce an average flow rate at 62 mmHg of greater than 2 Lpm, greater than 2.5 Lpm, greater than 3 Lpm, greater than 3.5 Lpm, greater than 4 Lpm, greater than 4.25 Lpm, greater than 4.5 Lpm, greater than 5 Lpm, greater than 5.5 Lpm, or greater than 6 Lpm.

Various aspects of the pump and associated components can be combined with or substituted for those disclosed in U.S. Pat. Nos. 7,393,181; 8,376,707; 7,841,976; 7,022,100; and 7,998,054, and in U.S. Pub. Nos. 2011/0004046; 2012/0178986; 2012/0172655; 2012/0178985; and 2012/0004495, the entire contents of each of which are incorporated herein for all purposes by reference. In addition, this application incorporates by reference in its entirety and for all purposes the subject matter disclosed in each of the following applications: U.S. Patent Publication No. US 2013/0303970, entitled "DISTAL BEARING SUPPORT," filed on Mar. 13, 2013; U.S. Patent Publication No. US 2014/0275725, entitled "FLUID HANDLING SYSTEM," filed on Mar. 11, 2014; U.S. Patent Publication No. US 2013/0303969, entitled "SHEATH SYSTEM FOR CATHETER PUMP," filed on Mar. 13, 2013; U.S. Patent Publication No. US 2013/0303830, entitled "IMPELLER FOR CATHETER PUMP," filed on Mar. 13, 2013; U.S. Patent Publication No. US 2014/0012065, entitled "CATHETER PUMP," filed on Mar. 13, 2013; and U.S. Patent Publication No. US 2014/0010686, entitled "MOTOR ASSEMBLY FOR CATHETER PUMP," filed on Mar. 13, 2013.

Moving from a distal end 1450 of the catheter assembly 101 of the catheter pump 100A of FIG. 1B to a proximal end 1455, a priming apparatus 1400 can be disposed over the impeller assembly 116A. As explained above, the impeller assembly 116A can include an expandable cannula or housing and an impeller with one or more blades. As the impeller rotates, blood can be pumped proximally (or distally in some implementations) to function as a cardiac assist device.

In FIG. 1B the priming apparatus 1400 can be disposed over the impeller assembly 116A near the distal end portion 170A of the elongate body 174A. The priming apparatus 1400 can be used in connection with a procedure to expel air from the impeller assembly 116A, e.g., any air that is trapped within the housing or that remains within the elongate body 174A near the distal end 170A. For example, the priming procedure may be performed before the pump is inserted into the patient's vascular system, so that air bubbles are not allowed to enter and/or injure the patient. The priming apparatus 1400 can include a primer housing 1401 configured to be disposed around both the elongate body 174A and the impeller assembly 116A. A sealing cap 1406 can be applied to the proximal end 1402 of the primer housing 1401 to substantially seal the priming apparatus 1400 for priming, i.e., so that air does not proximally enter the elongate body 174A and also so that priming fluid does not flow out of the proximal end of the housing 1401. The sealing cap 1406 can couple to the primer housing 1401 in any way known to a skilled artisan. In some embodiments, the sealing cap 1406 is threaded onto the primer housing by way of a threaded connector 1405 located at the proximal end 1402 of the primer housing 1401. The sealing cap 1406 can include a sealing recess disposed at the distal end of the sealing cap 1406. The sealing recess can be configured to allow the elongate body 174A to pass through the sealing cap 1406.

The priming operation can proceed by introducing fluid into the sealed priming apparatus 1400 to expel air from the impeller assembly 116A and the elongate body 174A. Fluid can be introduced into the priming apparatus 1400 in a variety of ways. For example, fluid can be introduced distally through the elongate body 174A into the priming apparatus 1400. In other embodiments, an inlet, such as a luer, can optionally be formed on a side of the primer housing 1401 to allow for introduction of fluid into the priming apparatus 1400. A gas permeable membrane can be disposed on a distal end 1404 of the primer housing 1401. The gas permeable membrane can permit air to escape from the primer housing 1401 during priming.

The priming apparatus 1400 also can advantageously be configured to collapse an expandable portion of the catheter pump 100A. The primer housing 1401 can include a funnel 1415 where the inner diameter of the housing decreases from distal to proximal. The funnel may be gently curved such that relative proximal movement of the impeller housing causes the impeller housing to be collapsed by the funnel 1415. During or after the impeller housing has been fully collapsed, the distal end 170A of the elongate body 174A can be moved distally relative to the collapsed housing. After the impeller housing is fully collapsed and retracted into the elongate body 174A of the sheath assembly, the catheter pump 100A can be removed from the priming housing 1400 before a percutaneous heart procedure is performed, e.g., before the pump 100A is activated to pump blood. The embodiments disclosed herein may be implemented such that the total time for infusing the system is minimized or reduced. For example, in some implementations, the time to fully infuse the system can be about six minutes or less. In other implementations, the time to infuse can be about three minutes or less. In yet other implementations, the total time to infuse the system can be about 45 seconds or less. It should be appreciated that lower times to infuse can be advantageous for use with cardiovascular patients.

With continued reference to FIG. 1B, the elongate body 174A extends from the impeller assembly 116A in a proximal direction to an fluid supply device 195. The fluid supply device is configured to allow for fluid to enter the catheter assembly 101 of the catheter pump 100A and/or for waste fluid to leave the catheter assembly 101 of the catheter pump 100A. A catheter body 120A (which also passes through the elongate body 174A) can extend proximally and couple to the motor assembly 1. As discussed in more detail herein, the motor assembly 1 can provide torque to a drive shaft that extends from the motor assembly 1 through the catheter body 120A to couple to an impeller shaft at or proximal to the impeller assembly 116A. The catheter body 120A can pass within the elongate body 174A such that the external elongate body 174A can axially translate relative to the internal catheter body 120A.

Further, as shown in FIG. 1B, a fluid supply line 6 can fluidly couple with the console 122 to supply saline or other fluid to the catheter pump 100A. The saline or other fluid can pass through an internal lumen of the internal catheter body 120A and can provide lubrication to the impeller assembly 116A and/or chemicals to the patient. The supplied fluid (e.g., saline or glucose solution) can be supplied to the patient by way of the catheter body 120 at any suitable flow rate. For example, in various embodiments, the fluid is supplied to the patient at a flow rate in a range of 15 mL/hr to 50 mL/hr, or more particularly, in a range of 20 mL/hr to 40 mL/hr, or more particularly, in a range of 25 mL/hr to 35 mL/hr. One or more electrical conduits 124 can provide electrical communication between the console 122 and the motor assembly 1. A controller within the console 122 can control the operation of the motor assembly 1 during use.

In addition, a waste line 7 can extend from the motor assembly 1 to a waste reservoir 126. Waste fluid from the catheter pump 100A can pass through the motor assembly 1 and out to the reservoir 126 by way of the waste line 7. In various embodiments, the waste fluid flows to the motor assembly 1 and the reservoir 126 at a flow rate which is lower than that at which the fluid is supplied to the patient. For example, some of the supplied fluid may flow out of the catheter body 120 and into the patient by way of one or more bearings. The waste fluid (e.g., a portion of the fluid which passes proximally back through the motor from the patient) may flow through the motor assembly 1 at any suitable flow rate, e.g., at a flow rate in a range of 5 mL/hr to 20 mL/hr, or more particularly, in a range of 10 mL/hr to 15 mL/hr.

Access can be provided to a proximal end of the catheter assembly 101 of the catheter pump 100A prior to or during use. In one configuration, the catheter assembly 101 is delivered over a guidewire 235. The guidewire 235 may be conveniently extended through the entire length of the catheter assembly 101 of the catheter pump 100A and out of a proximal end 1455 of the catheter assembly 101. In various embodiments, the connection between the motor assembly 1 and the catheter assembly 101 is configured to be permanent, such that the catheter pump, the motor housing and the motor are disposable components. However, in other implementations, the coupling between the motor housing and the catheter assembly 101 is disengageable, such that the motor and motor housing can be decoupled from the catheter assembly 101 after use. In such embodiments, the catheter assembly 101 distal of the motor can be disposable, and the motor and motor housing can be re-usable.

In addition, FIG. 1B illustrates the guidewire 235 extending from a proximal guidewire opening 237 in the motor assembly 1. Before inserting the catheter assembly 101 of the catheter pump 100A into a patient, a clinician may insert the guidewire 235 through the patient's vascular system to the heart to prepare a path for the impeller assembly 116A to the heart. In some embodiments, the catheter pump 100A can include a guidewire guide tube 20 (see FIG. 3) passing through a central internal lumen of the catheter pump 100A from the proximal guidewire opening 237. The guidewire guide tube 20 can be pre-installed in the catheter pump 100A to provide the clinician with a preformed pathway along which to insert the guidewire 235.

In one approach, the guidewire 235 is first placed through a needle into a peripheral blood vessel, and along the path between that blood vessel and the heart and into a heart chamber, e.g., into the left ventricle. Thereafter, a distal end opening of the catheter pump 100A and guidewire guide tube 20 can be advanced over the proximal end of the guidewire 235 to enable delivery to the catheter pump 100A. After the proximal end of the guidewire 235 is urged proximally within the catheter pump 100A and emerges from the guidewire opening 237 and/or guidewire guide tube 20, the catheter pump 100A can be advanced into the patient. In one method, the guidewire guide tube 20 is withdrawn proximally while holding the catheter pump 100A.

Alternatively, the clinician can thus insert the guidewire 235 through the proximal guidewire opening 237 and urge the guidewire 235 along the guidewire guide tube. The clinician can continue urging the guidewire 235 through the patient's vascular system until the distal end of the guidewire 235 is positioned in the desired position, e.g., in a chamber of the patient's heart, a major blood vessel or other source of blood. As shown in FIG. 1B, a proximal end portion of the guidewire 235 can extend from the proximal guidewire opening 237. Once the distal end of the guidewire 235 is positioned in the heart, the clinician can maneuver the impeller assembly 116A over the guidewire 235 until the impeller assembly 116A reaches the distal end of the guidewire 235 in the heart, blood vessel or other source of blood. The clinician can remove the guidewire 235 and the guidewire guide tube. The guidewire guide tube can also be removed before or after the guidewire 235 is removed in some implementations.

After removing at least the guidewire 235, the clinician can activate the motor 1 to rotate the impeller and begin operation of the pump 100A.

Figure 2:
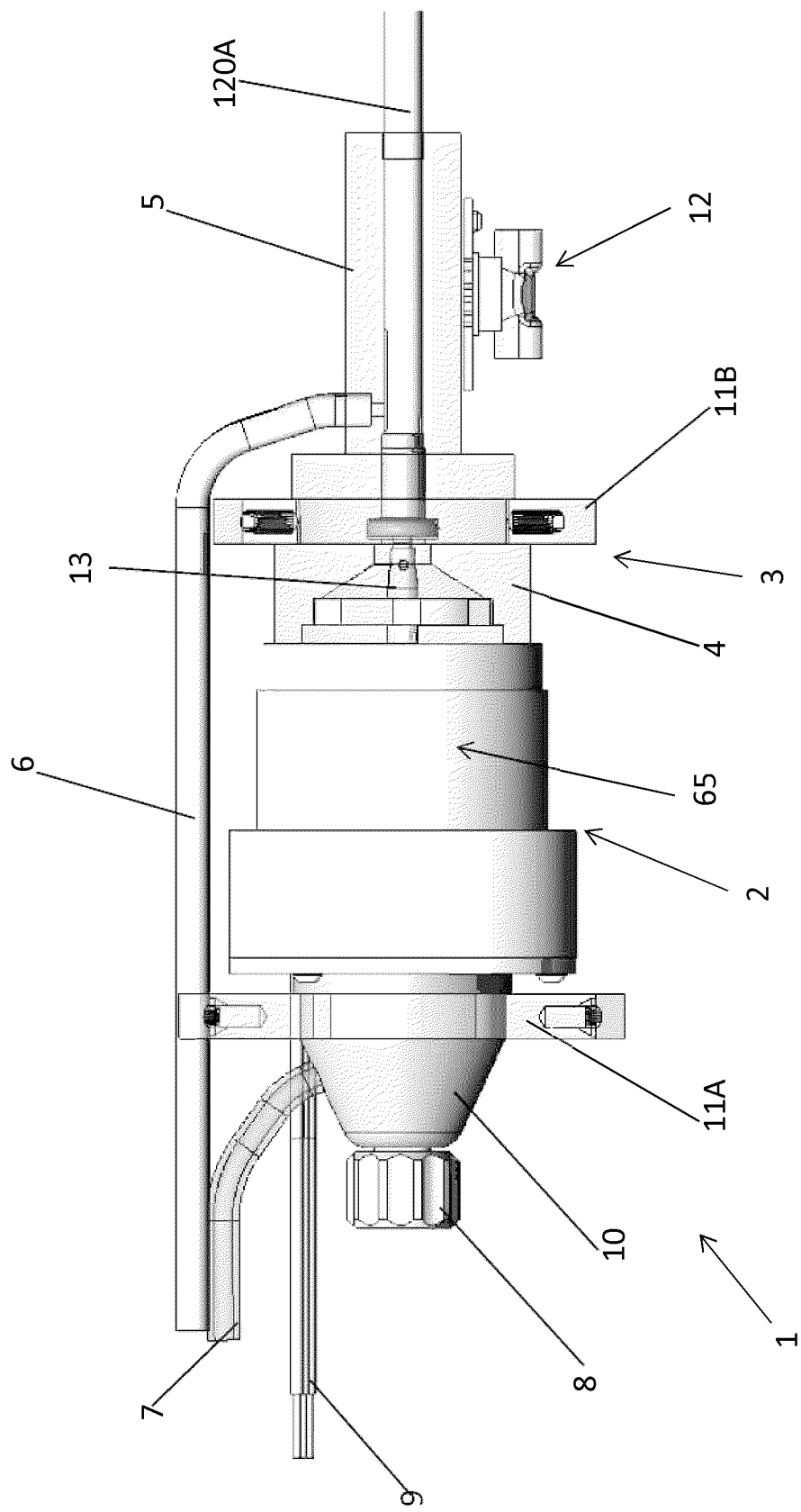
FIG. 2 is a side plan view of a motor assembly of the catheter pump system shown in FIG. 1B, according to various embodiments.
Figure 3:
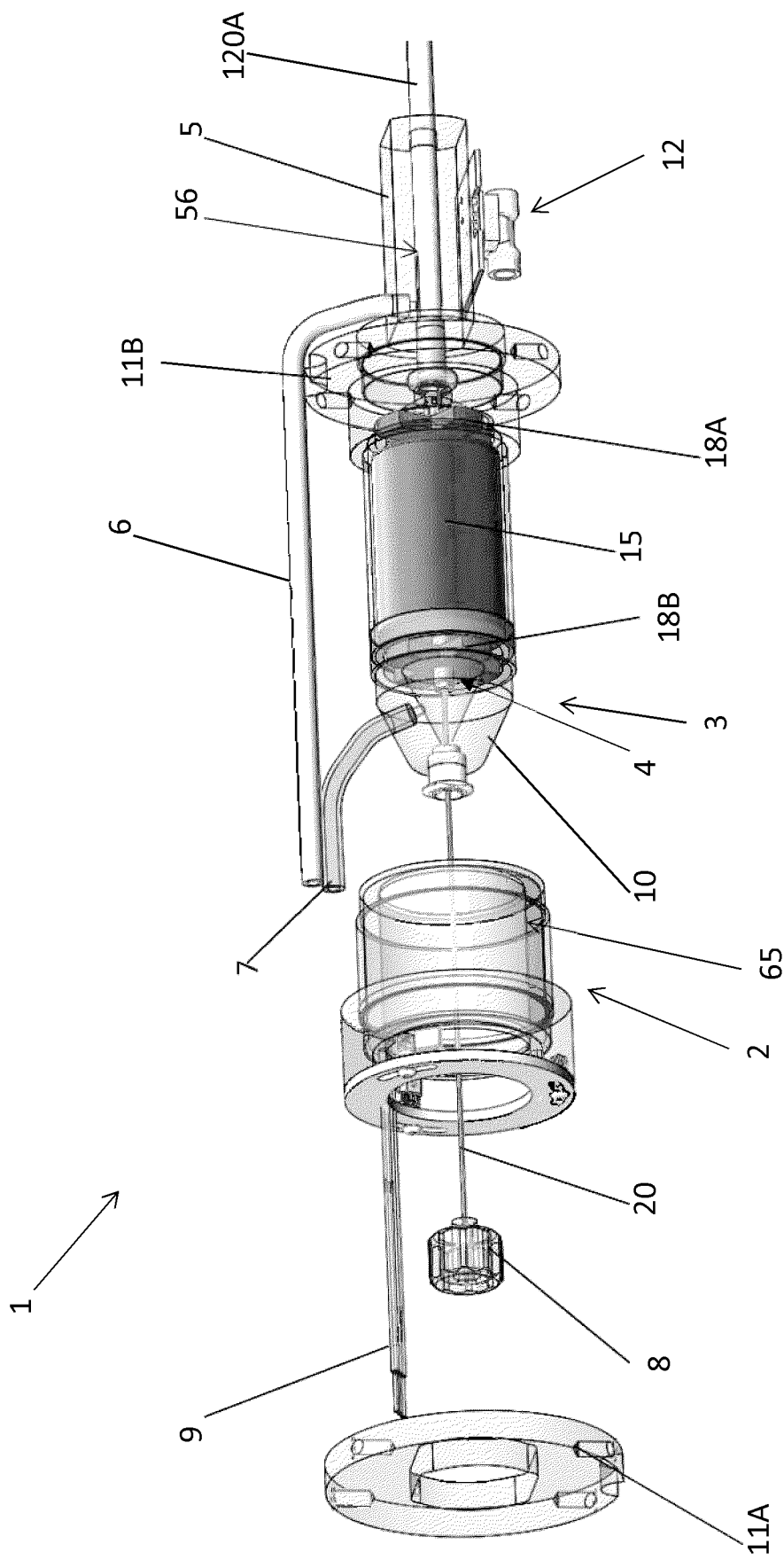
FIG. 3 is a perspective exploded view of the motor assembly shown in FIG. 2.

FIGS. 2 and 3 further illustrate aspects of embodiments of the motor assembly 1 shown in FIG. 1B. The motor assembly 1 can include a stator assembly 2 (FIGS. 2-3) and a rotor 15 disposed radially within the stator assembly 2 (FIG. 3). The motor assembly 1 also includes a flow diverter 3, which can be configured as a manifold for directing fluid through one or more passages in the catheter pump 100A. In some cases, the flow diverter 3 is at least partially disposed radially between the stator assembly 2 and the rotor 15 (FIGS. 2-3). The flow diverter 3 can be fluidly sealed about the rotor 15 and a proximal portion 56 of the catheter body 120A. The seal prevents leakage and also can prevent the fluid from contacting the stator assembly 2. The flow diverter 3 can include a distal chamber 5 within which the proximal portion 56 of the catheter body 120A is disposed and a rotor chamber 4 within which the rotor 15 is disposed. The flow diverter 3 can also have a proximal chamber 10 in some embodiments. Where provided, the distal chamber 5, rotor chamber 4, and proximal chamber 10 can be in fluid communication within the flow diverter 3. One or more flanges 11A, 11B can mechanically couple the flow diverter 3 to an external housing (not shown). The flanges 11A, 11B are examples of mount structures that can be provided, which can include in various embodiments dampers to isolate the motor assembly 1 from external shock or vibration. In some embodiments, mount structures can include dampers configured to isolate an outer housing or the environment external to the motor assembly 1 from shock or vibration generated by the motor assembly 1. Further, a pressure sensor assembly 12 is configured to measure the pressure at a distal portion of the catheter pump 100A by, for example, measuring the pressure of a column of fluid that extends distally through a lumen of the catheter body 120A. In addition, the guidewire guide tube 20 can extend proximally through the motor assembly 1 and can terminate at a tube end cap 8. As explained above, the guidewire 235 can be inserted within the guide tube 20 for guiding the catheter pump 100A to the heart.

The rotor 15 and stator assembly 2 can be configured as or be components of a frameless-style motor for driving the impeller assembly 116A at the distal end of the pump 100A. For example, the stator assembly 2 can comprise a stator and a plurality of conductive windings producing a controlled magnetic field. The windings can be wrapped about or in a stationary portion 65 of the stator assembly 2. The rotor 15 can comprise a magnetic material, e.g., can include one or more permanent magnets. In some embodiments, the rotor 15 can comprise a multi-pole magnet, e.g., a four-pole or six-pole magnet. Providing changing electrical currents through the windings of the stator assembly 2 can create magnetic fields that interact with the rotor 15 to cause the rotor 15 to rotate. This is commonly referred to as commutation. The console 122 can provide electrical power (e.g., 24V) to the stator assembly 2 to drive the motor assembly 1. One or more leads 9 can electrically communicate with the stator assembly 2, e.g., with one or more Hall sensors used to detect the speed and/or position of the motor. In other embodiments, other sensors (e.g., optical sensors) can be used to measure motor speed. The rotor 15 can be secured to an output shaft 13 (which can comprise a hollow shaft with a central lumen) such that rotation of the rotor 15 causes the output shaft 13 to rotate. In various embodiments, the motor assembly 1 can comprise a direct current (DC) brushless motor. In other embodiments, other types of motors can be used, such as AC motors, etc. As shown in FIG. 3, first and second journal bearings 18A, 18B can be provided about the output shaft 13 to radially and/or longitudinally center the output shaft 13 and thereby the rotor 15 relative to the stator assembly 2.

Figure 4A:
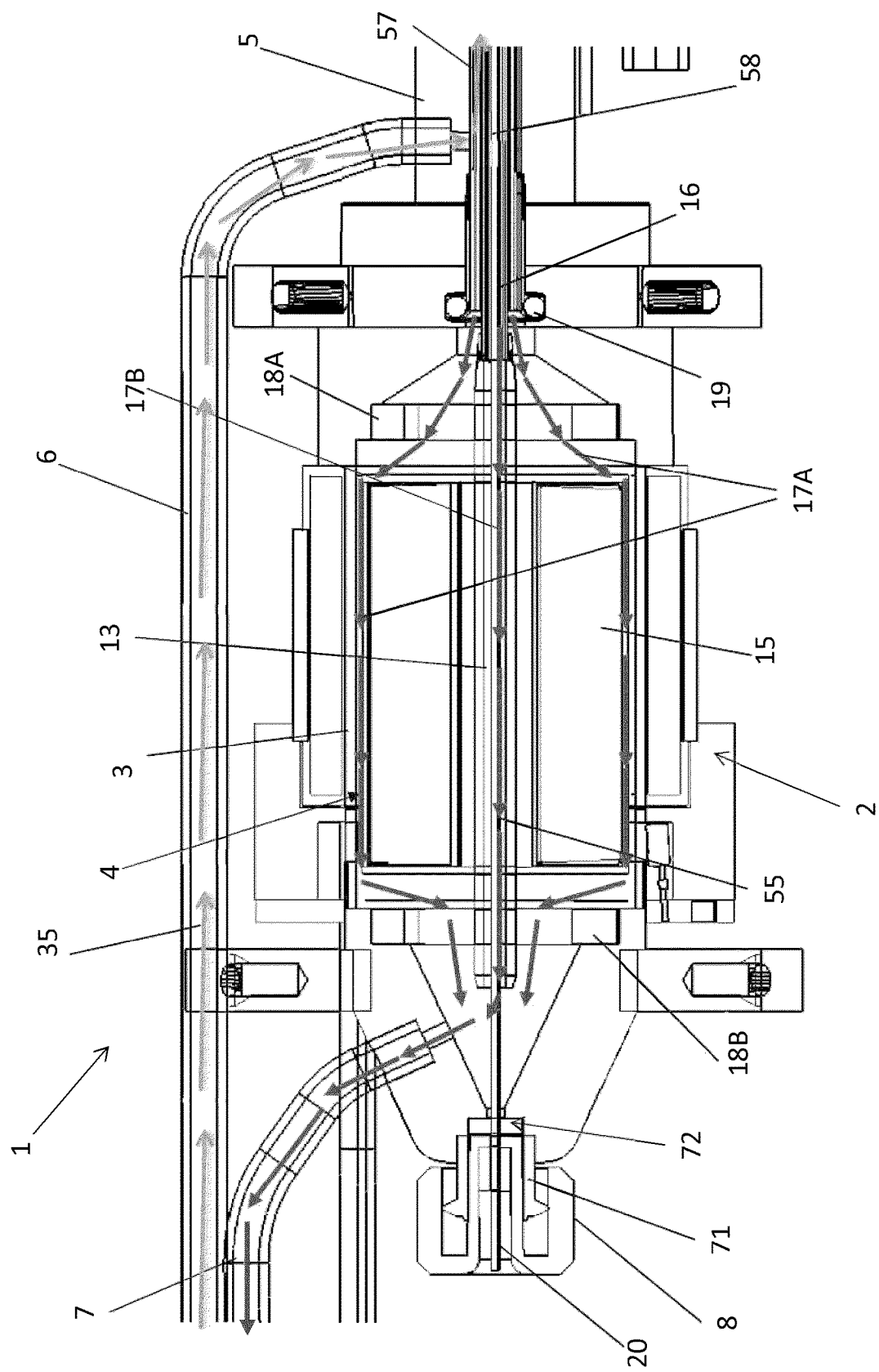
FIG. 4A is a side cross-sectional view of the motor assembly shown in FIGS. 2-3.

FIG. 4A shows that the output shaft 13 (which is secured to the rotor 15) can be mechanically coupled with the proximal end portion of a drive shaft 16. The drive shaft 16 extends distally through an internal lumen of the catheter body 120A. A distal end portion of the drive shaft 16 is mechanically connected with the impeller. Thus, rotation of the rotor 15 causes the output shaft 13 to rotate, which, in turn, causes the drive shaft 16 and the impeller to rotate. FIG. 4A also shows that a lumen 55 can extend through the output shaft 13 and the rotor 15. In certain embodiments, the lumen 55 is coupled with a lumen of the catheter body 120A such that the guidewire guide tube 20 can extend through the lumen 55 within the rotor 15 and into the lumen of the catheter body 120A. In addition, the drive shaft 16 comprises a braided shaft having an internal lumen. The braided drive shaft 16 or cable can be permeable to liquid such that supply fluid or waste fluid can flow from outside the drive shaft 16 to within the internal lumen of the drive shaft 16 (and vice versa).

Figure 7:
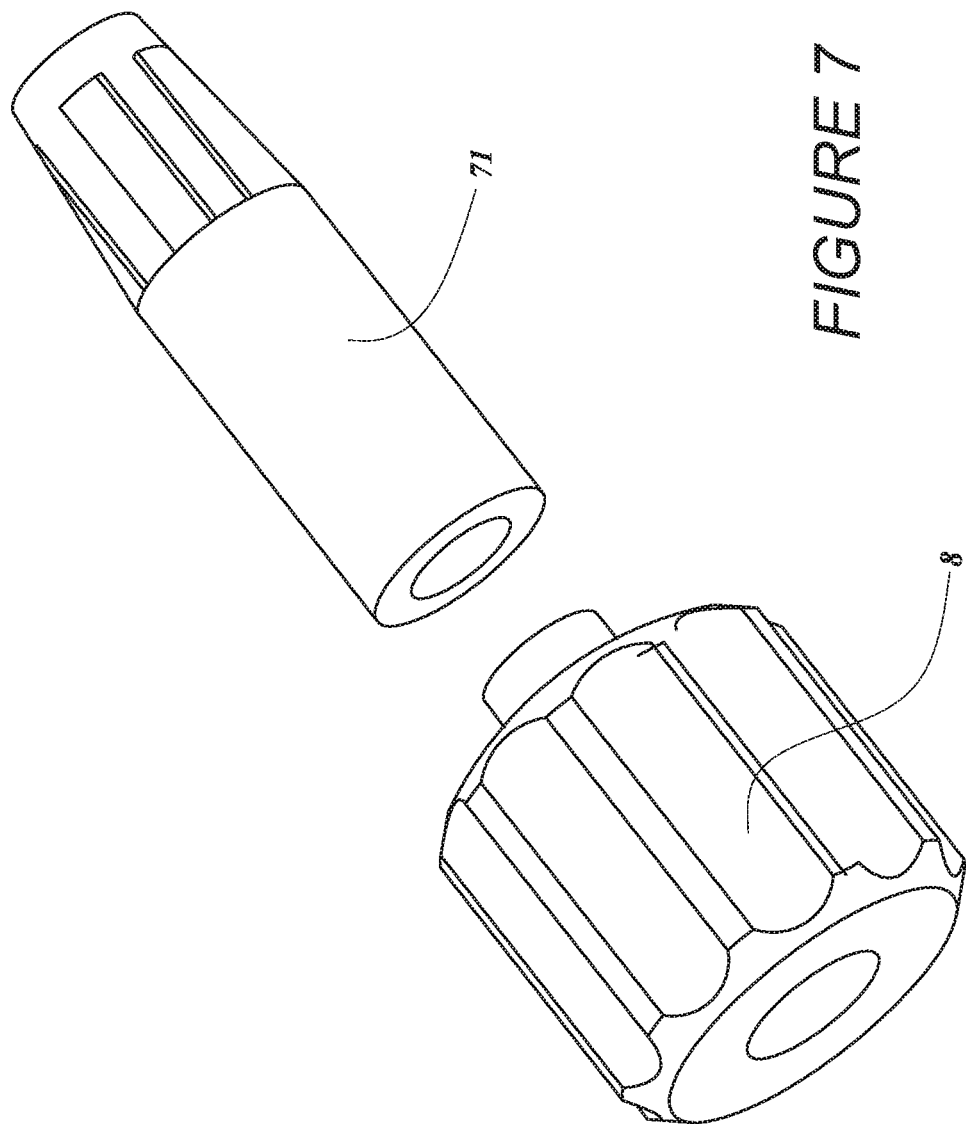
FIG. 7 is an image of a cap and a female receiver, with the guide tube not shown.

FIG. 4A shows the tube end cap 8 welded or otherwise secured to a proximal end portion of the guide tube 20. The cap 8 can be removably engaged (e.g., screwed or otherwise removably locked) over a female receiver 71 that is secured in a proximal end of the proximal chamber 10. For example, the proximal end of the female receiver 71 can be disposed in a counterbore of the cap 8, while the guide tube 20 extends through the central opening of the cap 8. In a locked configuration, one or more tabs of the receiver 71 can be rotated such that the tab(s) slide under a corresponding tab in the counterbore of the cap 8. In an unlocked configuration, the tab(s) of the receiver 71 can be rotated relative to the tabs of the cap 8. FIG. 7 shows one embodiment of the cap 8 and of the female receiver 71 that can be coupled with the guide tube 20 (not shown). In the illustrated embodiment, the cap 8 can be fixed to the guide tube 20; in other embodiments, the receiver 71 can be fixed to the guide tube 20. Engaging the cap 8 to the receiver 71 can advantageously prevent the guide tube 20 from accidentally being removed from or slid within the catheter pump 100A, e.g., if the patient or clinician impacts the cap 8. To remove the guide tube 20 (e.g., after delivery of the impeller assembly 116A to the heart), the clinician can disengage the cap 8 from the receiver 71 and can pull the guide tube 20 from the catheter pump 100A, for example, by pulling proximally on the end cap 8. A resealable septum 72 (e.g., a resealable closure member) can be provided at the proximal end of the flow diverter 3, e.g., near the distal end of the cap 8 when the cap 8 is in place. When the guidewire guide tube 20 is removed from the pump 100A, the septum 72 will naturally reseal the pathway proximally from the motor assembly 1 such that fluid does not exit the assembly 1. An advantage of the assembly described herein is that the cap 8 is locked and will not be dislodged without rotating and unlocking cap 8 from receiver 71. With a conventional torquer assembly, the cap 8 can slide axially if it is inadvertently bumped by the patient or clinician. This potentially results in the guide tube 20 being pulled out from the distal-most end of the impeller assembly 116A, and because the guide tube cannot be re-inserted, the clinician either has to use the catheter pump 100A without a guide or get a new pump.

With continued reference to FIG. 4A, it can be important to ensure that the motor assembly 1 is adequately cooled. In various embodiments, it can be important to provide a heat removal system to limit buildup of heat in the motor assembly 1 during operation. For example, it can be important to maintain external surfaces of the motor assembly 1 at a temperature less than about 40° C. if the motor assembly 1 is positioned near the patient. For example, an external surface of an external housing of the motor assembly 1 may be kept at or below this temperature. In some respects, regulatory guidelines can require that no part in contact with skin exceed 40° C. To that end, various strategies for heat management are employed by the inventions described herein. It should be appreciated that, as used herein, cooling refers to transferring away or dissipating heat, and in certain respects, cooling is used interchangeably with removing heat.

Various components of the motor assembly 1 generate heat. For example, moving parts within the motor assembly 1 (e.g., the rotating output shaft 13 and/or drive shaft 16) can generate heat by virtue of losses through friction, vibrations, and the like, which may increase the overall temperature of the motor assembly 1. Further, heat can be generated by the electrical current flowing through the stator assembly 2 and/or by induction heating caused by conductive components inside a rotating magnetic field. Furthermore, friction between the bearings 18 and the output shaft 13 and/or friction between the drive shaft 16 and the inner wall of catheter body 120A may also generate undesirable heat in the motor assembly. Inadequate cooling can result in temperature increases of the motor assembly 1, which can present patient discomfort, health risks, or performance losses. This can lead to undesirable usage limitations and engineering complexity, for example, by requiring mitigation for differential heat expansion of adjacent components of different materials. Accordingly, various embodiments disclosed herein can advantageously transfer away generated heat and cool the motor assembly 1 such that the operating temperature of the assembly 1 is sufficiently low to avoid such complexities of use or operation and/or other components of the system. For example, various heat transfer components can be used to move heat away from thermal generation sources and away from the patient. Various aspects of the illustrated device herein are designed to reduce the risk of hot spots, reduce the risk of heat spikes, and/or improve heat dissipation to the environment and away from the patient.

In some embodiments, the catheter pump makes use of the fluid supply system already embedded in the pump to cool the motor assembly 1 and housing. In some embodiments, heat absorbing capacity of fluid flowing through the flow diverter 3 is used to cool the motor assembly 1. As shown in FIG. 4A, the supply line 6 can supply fluid 35 from a source (e.g., a fluid bag) to an outer lumen 57 of the catheter body 120A. The supplied fluid 35 can travel distally toward the impeller assembly 116A to lubricate rotating components in the catheter assembly 101 and/or supply fluid to the patient. A seal 19 (e.g., an o-ring) can be provided between the rotor housing 4 and the distal housing 5 to prevent backflow of the fluid 35 into the rotor housing 4. In this context, backflow is flow of fluid 35 proximally into the distal housing 5 rather than distally within the lumen 57. Such flow is to be prevented to ensure that the fluid 35 is initially exposed to moving parts in a distal portion of the catheter assembly 101 to lubricate and cool such distal components.

Fluid from the catheter pump 100A can flow proximally through an inner lumen 58 of the catheter body 120A. For example, after initially cooling distal components some or all of the supplied fluid 35 can flow within the drive shaft 16 and/or around the periphery of the drive shaft 16. After initially cooling distal components some or all of the supplied fluid 35 can flow in a space disposed radially between the drive shaft 16 and the catheter body 120A. The proximally-flowing fluid can flow along a flow pathway which removes heat from the motor assembly 1. As shown in FIG. 4A, the proximally-flowing fluid (or other cooling fluid) can flow into the rotor chamber 4 of the flow diverter 3. A first portion 17A of the waste fluid can pass proximally through the motor assembly 1 about a periphery of the rotor 15, e.g., in a gap between the rotor 15 and a wall of the flow diverter 3. In some embodiments, a second portion 17B of the waste fluid can pass proximally through the motor assembly 1 through the lumen 55 of the output shaft 13. The fluid portions 17A, 17B can pass from the rotor chamber 4 into the proximal chamber 10 of the flow diverter 3, where the fluid 17A, 17B can flow out to a reservoir (not shown) by way of line 7.

The embodiment of FIG. 4A can advantageously convey heat from the heat generating components (e.g., rotor 15 and stator assembly 2) into the fluid 35 or other cooling fluid and to the reservoir 126 by way of the waste line 7. For example, the first portion 17A of the fluid that passes about the periphery of the rotor 15 can direct heat radially outward from the rotor 15 and other components of the flow diverter 3. The first portion 17A of the fluid that passes about the periphery of the rotor 15 can direct heat inward from the stator assembly 2 and other components outside the flow diverter 3. The second portion 17B of the waste fluid can draw heat radially inward, e.g., radially inward from the rotor 15 and other components of the flow diverter 3. As the heat from the motor assembly 1 is conveyed away by way of the fluid to the reservoir 126, the temperature of the motor housing can be reduced or maintained at a suitable operational temperature for the medical staff, the patient and/or for the catheter pump system. A gap between the stator assembly and the external motor housing (e.g., the outer shell or housing surrounding the motor assembly) comprises air, which is a good, natural insulator. Thus, the heat from the stator assembly 2 is naturally transferred to the waste line rather than dissipating out the sides of the housing of the motor assembly 1.

Figure 4B:
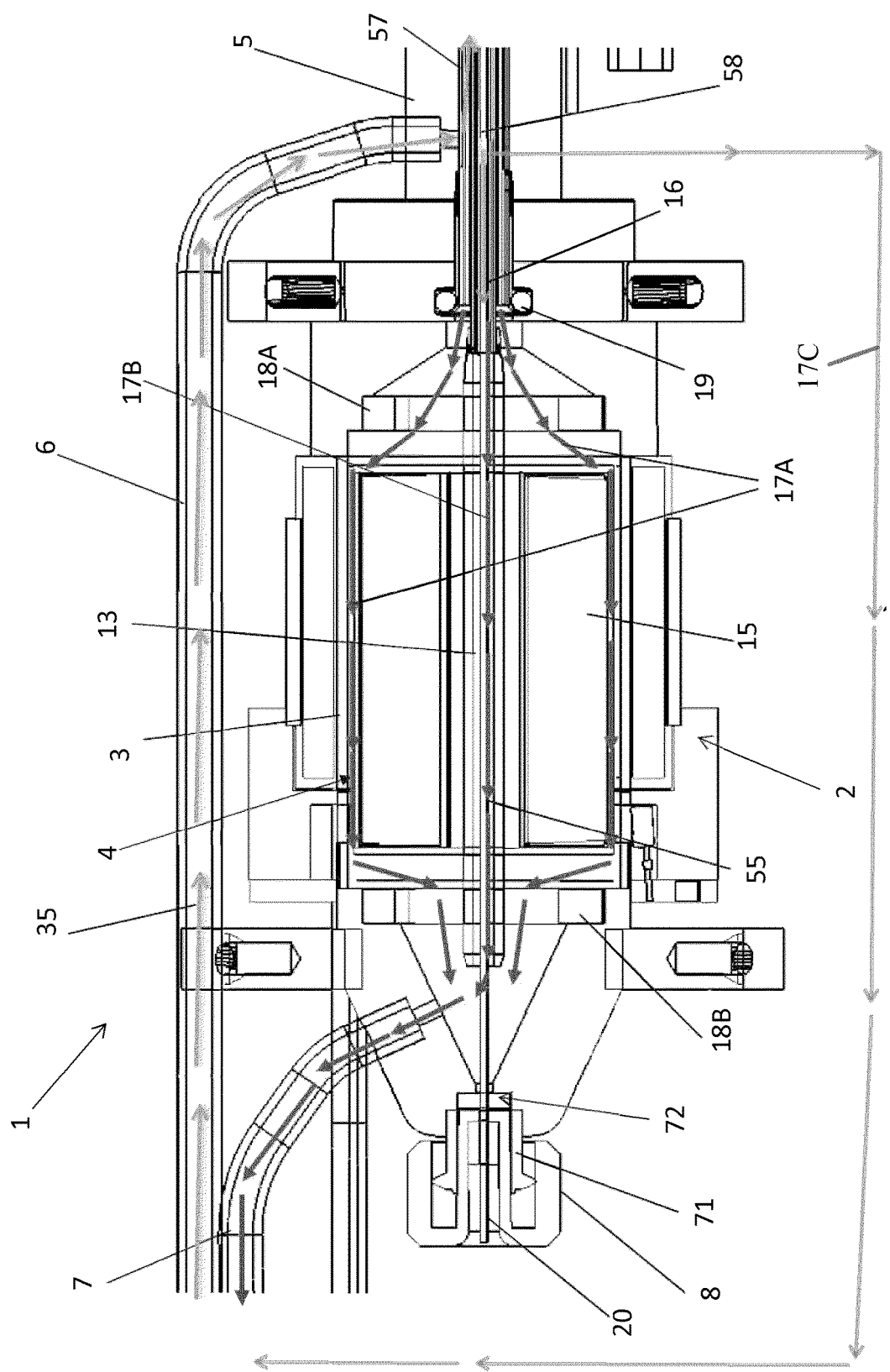
FIG. 4B is a side cross-sectional view of a motor assembly, according to another embodiment.

FIG. 4B is a side cross-sectional view of a motor assembly 1, according to another embodiment. Unless otherwise noted, components numbered similar to those in FIG. 4A represent the same or similar components and functionalities. For example, as with the embodiment of FIG. 4A, in the embodiment of FIG. 4A, a first portion 17A of the fluid can pass proximally through the motor assembly 1 about a periphery of the rotor 15, e.g., in a gap between the rotor 15 and a wall of the flow diverter 3. In some embodiments, a second portion 17B of the fluid can pass proximally through the motor assembly 1 through the lumen 55 of the output shaft 13. The fluid portions 17A, 17B can pass from the rotor chamber 4 into the proximal chamber 10 of the flow diverter 3, where the fluid 17A, 17B can flow out to a reservoir (not shown) by way of line 7. Thus, the fluid portions 17A, 17B can flow along a first fluid pathway or channel within the flow diverter 3 which is disposed inside the stator 2.

Unlike the embodiment of FIG. 4A, however, in the embodiment of FIG. 4B, a third portion 17C of the fluid can be shunted around the rotor 15 and stator assembly 2 along a second fluid pathway or channel. For example, as shown in FIG. 4B, the third portion 17C of the proximally-flowing fluid can be withdrawn from the inner lumen 58 of the catheter body 120A by way of a suitable conduit and fluid connector. The third fluid portion 17C can bypass the motor assembly 1 and can be conveyed to the waste reservoir by a suitable waste line, which may be the same as or different from the waste line 7. The third portion 17C of the proximally-flowing fluid can be more than, less than, or about the same in volume as the combined volume of the first and second fluid portions 17A, 17B. In other embodiments, rather than being conveyed directly to a waste line, the third portion 17C can be transported by a conduit to a heat exchanger to further cool the motor assembly 1. For example, the third fluid portion 17C can be conveyed to coiled tubing or a tubular sleeve disposed about the stator assembly 2, as shown in various embodiments of the following concurrently filed application: application Ser. No. 15/003,682, now issued U.S. Pat. No. 9,675,739, entitled "MOTOR ASSEMBLY WITH HEAT EXCHANGER FOR CATHETER PUMP," filed on the same date as this application and which is expressly incorporated by reference herein in its entirety and for all purposes.

The embodiment of FIG. 4B may be desirable in arrangements in which the first and second fluid portions 17A, 17B become too hot and/or otherwise ineffective at cooling the motor assembly 1. For example, in some arrangements, the motor assembly 1 may heat the first and second fluid portions 17A, 17B passing inside the flow diverter 3 to such a degree that the temperatures of the fluid portions 17A, 17B and/or the motor assembly 1 rise to unacceptable levels. In such a situation, it may be desirable to shunt some, most, or all of the proximally-flowing fluid around the motor assembly 1 along the second fluid pathway. For example, in some embodiments, the first and second fluid portions 17A, 17B may pass through the flow diverter 3 along the first fluid pathway at a flow rate less than that provided in the embodiment of FIG. 4A. In the embodiment of FIG. 4A, the fluid may flow back proximally through the flow diverter at rate such that the combined flow rate of the first and second portions 17A, 17B is in a range of 5 mL/hr to 20 mL/hr, or more particularly, in a range of 10 mL/hr to 15 mL/hr.

In the embodiment of FIG. 4B, however, some, most, or all of the proximally-flowing fluid is diverted around the flow diverter 3 and other components of the motor along the second fluid pathway as the third fluid portion 17C. The amount of the fluid portion 17C diverted around the motor assembly 1 can be any suitable amount so as to maintain an adequate external temperature of the motor housing 1. For example, in one embodiment, the third fluid portion 17C represents a relatively small volume of fluid diverted from the inner lumen 58. In one embodiment, the third fluid portion 17C flows around the motor assembly 1 at a flow rate in a range of 1 mL/hr to 30 mL/hr. In one embodiment, the third fluid portion 17C flows around the motor assembly 1 at a flow rate in a range of 1 mL/hr to 5 mL/hr, or in a range of 1 mL/hr to 3 mL/hr. In one embodiment, the third fluid portion 17C flows around the motor assembly 1 at a flow rate in a range of 10 mL/hr to 50 mL/hr. In another embodiment, the third fluid portion 17C represents a majority of the fluid diverted from the inner lumen 58. For example, in such an embodiment, the third fluid portion 17C may have a flow rate in a range of 5.5 mL/hr to 12 mL/hr, in a range of 5.5 mL/hr to 10 mL/hr, in a range of 5.5 mL/hr to 8 mL/hr, in a range of 5.5 mL/hr to 7 mL/hr, in a range of 10 mL/hr to 14 mL/hr, or in a range of 8 mL/hr to 12 mL/hr. Advantageously, diverting some of the proximally-flowing fluid around the motor assembly 1 can improve the transfer of heat away from the motor assembly 1, for example, in situations in which the first and second fluid portions 17A, 17B become too hot.

Moreover, in some embodiments, the console 122 can be configured to change the amount of the third fluid portion 17C flowing along the second fluid pathway before and/or during a treatment procedure to adjust the volume of fluid that is diverted from the inner lumen 58 around the motor assembly 1. For example, the console 122 can send instructions to a pump (such as a peristaltic pump) to adjust the flow rate of fluid shunted around the motor assembly 1. In some embodiments, a common pump is applied to all three fluid portions 17A-17C. In other embodiments, one pump is applied to draw the first and second fluid portions 17A, 17B, and a separate pump is applied to draw the third fluid portion 17C.

In still other embodiments, all or substantially all the fluid flowing proximally through the inner lumen 58 is shunted around the motor assembly 1 along the second fluid pathway. The shunted third fluid portion 17C can be diverted to a waste reservoir and/or to a heat exchanger disposed about the stator assembly 2, as explained above. In such embodiments, all (100%) or substantially all (i.e., between 90% and 100%) of the proximally-flowing fluid does not flow within the motor assembly 1 (e.g., within the flow diverter 3), but is instead diverted around the motor assembly 1. Thus, in some embodiments, there may be no proximally-flowing fluid portions 17A, 17B within the flow diverter 3. In such arrangements, the motor assembly 1 may be adequately cooled without the fluid portions 17A, 17B flowing proximally through the flow diverter 3. The fluid flowing proximally through the inner lumen 58 may also provide sufficient pressure so as to prevent air or other gases from passing distally through the catheter body 120A to the patient.

Advantageously, the embodiments disclosed in FIGS. 1A-4B can adequately remove heat from the motor assembly 1 without requiring the use of external cooling fins exposed to the outside environs. That is, the thermal performance of the heat removal systems disclosed in FIGS. 2-4B can adequately reduce the temperature of the outer surface of the motor housing without using cooling fins exposed outside of the motor housing (e.g., outside of an exterior surface of the motor assembly 1) to the ambient environment. Rather, the heat removal systems may be disposed entirely within the motor housing, e.g., within the housing which encloses the rotor and stator. For example, in some embodiments, the systems disclosed in FIGS. 1A-4B can ensure that the temperature of the exterior surface of the motor assembly 1 is not more than about 40° C. In some embodiments, the systems disclosed in FIGS. 1A-4B can ensure that the temperature of the exterior surface of the motor assembly 1 is in a range of 15° C. to 42° C., or more particularly in a range of 20° C. to 42° C., in a range of 20° C. to 40° C., in a range of 20° C. to 35° C., or in a range of 20° C. to 30° C., without requiring the use of external cooling fins exposed outside the motor housing.

Still other thermal management techniques may be suitable in combination with the embodiments disclosed herein. For example, U.S. Patent Publication Nos. 2014/0031606 and 2011/0295345, which are incorporated by reference herein in their entirety and for all purposes, describe structures and materials which may be incorporated in place of or in addition to the devices described above to dissipate heat effectively, as will be understood by one of skill from the description herein.

Figure 5:
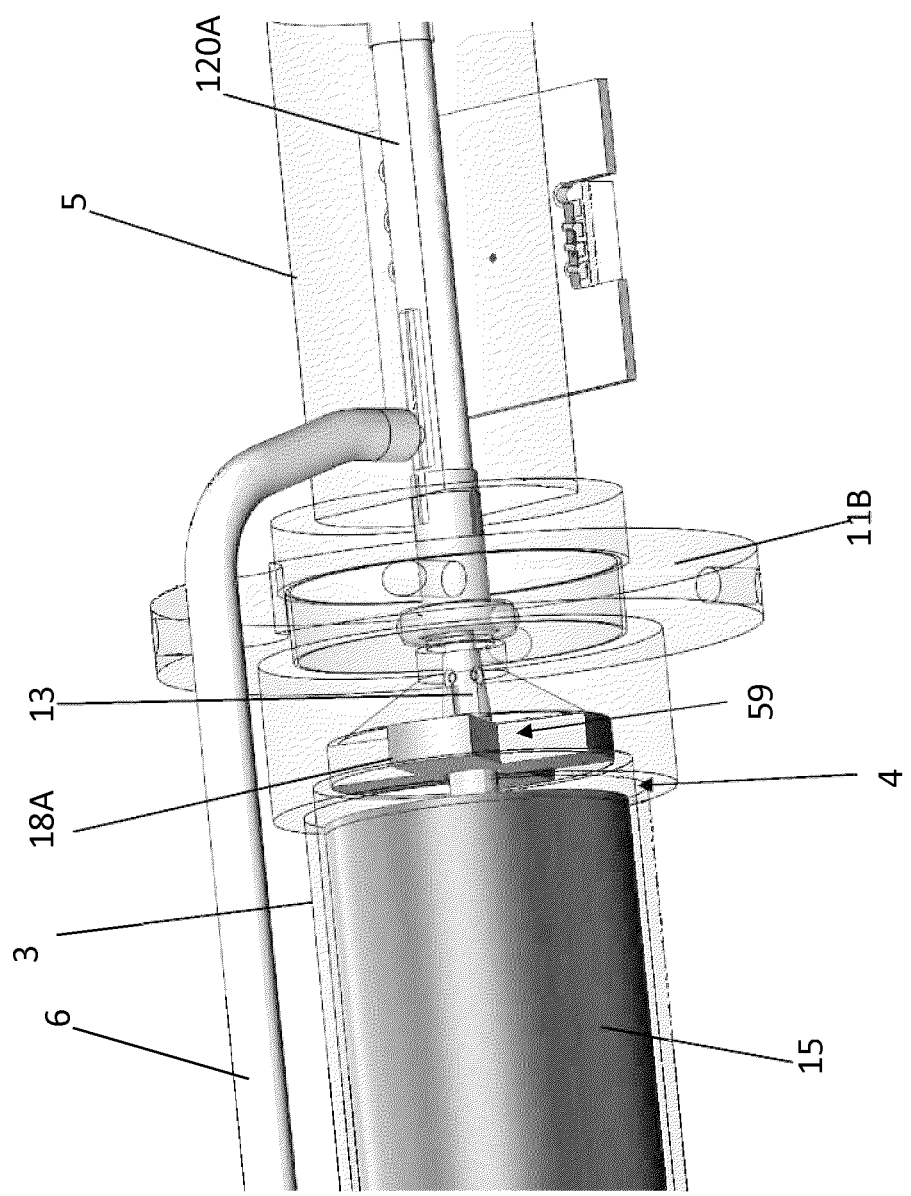
FIG. 5 is a schematic perspective view of an interface between a distal chamber and a rotor chamber of a flow diverter of the motor assembly, with a stator assembly thereof hidden for ease of illustration.

FIG. 5 is a schematic perspective view of an interface between the distal chamber 5 and the rotor chamber 4 of the flow diverter 3, with the stator assembly 2 hidden for ease of illustration. FIG. 5 shows the output shaft 13 coupled with a proximal portion of the drive shaft 16 through an aperture in the flange 11B. The journal bearings 18A (FIGS. 3 and 5) and 18B (FIG. 3) can be provided on opposite axial sides of the rotor 15 to help maintain the rotor 15 in radial alignment with the rotor chamber 4 and in axial alignment with the stator assembly 2. Improving radial alignment of the rotor 15 and output shaft 13 relative to the rotor chamber 4 can reduce or eliminate eccentricity during rotation, which can reduce vibrations. Improving axial alignment relative to the stator assembly 2 can advantageously improve the efficiency of the motor assembly 1 by ensuring that the windings of the stator assembly 2 are adequately aligned with the rotor 15. In various embodiments, the journal bearings 18A, 18B can be rotationally decoupled with the output shaft 13 such that the output shaft 13 can rotate relative to the bearings 18A, 18B. In some embodiments, the journal bearings 18A, 18B can be fixed inside the rotor chamber 4. Moreover, one or more passages 59 can be provided through or across the bearings 18A, 18B so that cooling fluid can pass axially through the bearings 18A, 18B. For example, as shown in FIG. 5, the passages 59 are defined at least in part by a cross-shaped structure of the bearings 18A, 18B, but other variations for the openings 59 may be suitable. For example, the bearings 18A, 18B can form radially-extending arms with one or more gaps disposed between the arms. Such gaps can be enclosed peripherally by a housing enclosing the stator assembly 2. In other embodiments, one or more openings can be provided through the bearings 18A, 18B to define the passages.

FIGS. 6A and 6B show one embodiment of an interface 22 between the output shaft 13 and the drive shaft 16. The interface 22 can comprise a connection between a distal portion of the output shaft 13 and a proximal portion of the drive shaft 16. The distal portion of the output shaft 13 can comprise a radially-inward taper and one or more holes 61 formed through the output shaft 13. The proximal portion of the drive shaft 16 can be inserted within the lumen 55 of the output shaft 13 such that the lumen 55 and the inner lumen 58 of the catheter body 120A form a continuous passage.

This passage can be used to advance the guidewire guide tube 20, sensors, and other instruments, or to provide fluid communication for cooling fluid or medications. Cooling fluid can flow proximally from the inner lumen 58 of the catheter body 120 and the first portion 17A of the fluid can pass outwardly about the periphery of the rotor 15. In some embodiments, the second portion 17B of the fluid can pass through the lumen 55 of the output shaft 13. A sleeve 21 can be disposed about the proximal portion of the catheter body 120A, and the seal 19 can be provided about the seal 21 to seal the distal chamber 5 from the rotor chamber 4.

In the illustrated embodiments, the output shaft 13 is permanently coupled with, e.g., laser welded to the drive shaft 16. For example, a welding machine can access the interface 22 by way of the holes 61 formed in the output shaft 13 to weld the output shaft 13 to the drive shaft 16. In other embodiments, the output shaft 13 can be secured to the drive shaft 16 in other ways, e.g., by friction or interference fit, by adhesives, by mechanical fasteners, etc.

Although the embodiments disclosed herein have been described with reference to particular embodiments, it is to be understood that these embodiments are merely illustrative of the principles and applications of the present inventions. It is therefore to be understood that numerous modifications can be made to the illustrative embodiments and that other arrangements can be devised without departing from the spirit and scope of the present inventions as defined by the appended claims. Thus, it is intended that the present application cover the modifications and variations of these embodiments and their equivalents.

What is claimed is:

1. A catheter pump system comprising:
   an impeller;
   a catheter body;
   a drive shaft disposed inside the catheter body and coupled with the impeller at a distal portion of the drive shaft, the drive shaft configured such that rotation of the drive shaft causes the impeller to rotate; and
   a motor assembly comprising:
      a chamber, at least a portion of the chamber in fluid communication with the catheter body, wherein a portion of the drive shaft is disposed in the at least a portion of the chamber;
      a rotor disposed in the at least a portion of the chamber;
      a stator assembly disposed about the drive shaft and configured to cause the drive shaft to rotate, wherein the catheter body extends from the motor assembly towards the impeller, the motor assembly disposed at a proximal portion of the catheter body; and
      a longitudinal rotor lumen disposed through the rotor such that the longitudinal rotor lumen extends on the proximal and distal sides of the rotor, wherein during operation of the catheter pump system, fluid flows through the longitudinal rotor lumen, through the rotor, and through the catheter body.

2. The catheter pump system of claim 1, wherein the rotor is mechanically coupled with a proximal portion of the drive shaft such that rotation of the rotor causes the drive shaft to rotate.

3. The catheter pump system of claim 2, wherein the stator assembly is disposed about the rotor.

4. The catheter pump system of claim 2, wherein the rotor comprises a magnetic material.

5. The catheter pump system of claim 4, wherein the rotor comprises a multi-pole magnet.

6. The catheter pump system of claim 2, further comprising first and second journal bearings positioned about the drive shaft to center the rotor relative to the stator assembly.

7. The catheter pump system of claim 2, further comprising a flow diverter at least partially disposed between the stator assembly and the rotor.

8. The catheter pump system of claim 1, wherein the catheter body comprises a lumen in which fluid flows proximally therethrough during operation of the catheter pump.

9. The catheter pump system of claim 8 wherein at least a portion of the chamber is in fluid communication with the lumen.

10. The catheter pump system of claim 1, wherein no cooling fins extend outside an exterior surface of the motor assembly.

11. The catheter pump system of claim 1, wherein the stator assembly comprises a stator and a plurality of conductive windings for producing a controlled magnetic field.

12. The catheter pump system of claim 11, wherein the plurality of conductive windings are in contact with a portion of the stator assembly.

13. The catheter pump system of claim 1, further comprising at least one lead and at least one sensor of the stator assembly, wherein the at least one lead is in electrical communication with the at least one sensor of the stator assembly.

14. The catheter pump system of claim 13, wherein the at least one sensor is configured to detect at least one of a speed and a position of the motor assembly.

15. The catheter pump system of claim 14, further comprising at least one flange configured to mechanically couple the flow diverter to an external housing.

16. The catheter pump system of claim 15, wherein the at least one flange operates as a damper to isolate components external to the motor assembly from vibrations generated by the motor assembly.

* * * * *